United States Patent
Allesee et al.

[11] Patent Number: 5,820,370
[45] Date of Patent: *Oct. 13, 1998

[54] PREADJUSTED ORTHODONTIC BRACKET SYSTEM AND METHOD

[75] Inventors: Timothy J. Allesee, Geneva; David J. Brosius, Crete, both of Ill.

[73] Assignee: Ortho Specialties, Hickory Hills, Ill.

[*] Notice: This patent issued on a continued prosecution application filed under 37 CFR 1.53(d), and is subject to the twenty year patent term provisions of 35 U.S.C. 154(a)(2).

[21] Appl. No.: 554,786

[22] Filed: Nov. 7, 1995

Related U.S. Application Data

[63] Continuation-in-part of Ser. No. 148,974, Nov. 8, 1993, Pat. No. 5,464,347.

[51] Int. Cl.⁶ ............................................. A61C 3/00
[52] U.S. Cl. ................................. 433/8; 433/20; 433/24
[58] Field of Search .................................. 433/8, 9, 24, 20

[56] References Cited

U.S. PATENT DOCUMENTS

| | | | |
|---|---|---|---|
| 3,477,128 | 11/1969 | Andrews | 433/24 X |
| 3,660,900 | 5/1972 | Andrews | 433/24 X |
| 5,474,448 | 12/1995 | Andreiko et al. | 433/24 |
| 5,588,833 | 12/1996 | Risse | 433/24 |

OTHER PUBLICATIONS

Dellinger, Eugene L., "A scientific assessment of the straight–wire appliance," *American Journal of Orthodontics*, vol. 73, No. 3, Mar. 1978, pp. 290–299.

Creekmore, Thomas D., et al., "Straight wire: The next generation," *American Journal of Orthodontics and Dentofacial Orthopedics*, vol. 104, No. 1, Jul. 1993, pp. 8–20.

*Primary Examiner*—Nicholas D. Lucchesi
*Attorney, Agent, or Firm*—Leydig, Voit & Mayer, Ltd.

[57] ABSTRACT

A preadjusted orthodontic bracket system for applying torque force to a selected tooth. The system comprises an archwire of substantially rectangular cross-section having first and second side dimensions and a bracket configured to be attached to the selected tooth and including a substantially rectangular slot which edgewise receives the archwire, the slot having a predetermined width and being formed in the bracket at a built-in torque angle. The smaller of the first and second side dimensions of the archwire is less than full-size for the width of the bracket slot and the built-in torque angle of the slot is greater than a full expression of a target torque angle recommended for the tooth by a selected one of the Roth, Andrews, Alexander, Hilgers, Bench, Ricketts, Cetlin and other known preadjusted orthodontic techniques. The archwire and preadjusted bracket, in combination, apply force to the tooth at an actual torque angle which substantially corresponds to the target torque angle recommended for the tooth by the selected orthodontic technique.

15 Claims, 14 Drawing Sheets

|     | ROTH | ANDREWS | ALEXANDER | HILGERS | BENCH | RICKETTS | CETLIN |
|-----|------|---------|-----------|---------|-------|----------|--------|
| U1  | +12  | +7      | +14       | +22     | +17   | +22      | +12    |
| U2  | +8   | +3      | +7        | +14     | +10   | +14      | +8     |
| U3  | -2   | -7      | -3        | +7      | +7    | +7       | -2     |
| U4  | -7   | -7      | -7        | -7      | -7    | 0        | -7     |
| U5  | -7   | -7      | -7        | -7      | -7    | 0        | -7     |
| U6  | -14  | -10     | -10       | -10     | -10   | 0        | -10    |
| U7  | -14  | -10     | -10       | -10     | -10   | 0        | -10    |
| L1  | -1   | -1      | -5        | -1      | -1    | 0        | 0      |
| L2  | -1   | -1      | -5        | -1      | -1    | 0        | 0      |
| L3  | -11  | -11     | -7        | +7      | +7    | +7       | -5     |
| L4  | -17  | -17     | -11       | -11     | -11   | 0        | -11    |
| L5  | -22  | -22     | -17       | -17     | -22   | -14      | -17    |
| L6  | -27  | -25     | -22       | -27     | -27   | -22      | -25    |
| L7  | -30  | -30     | -27       | -27     | -27   | -30      | -30    |

TORQUE ANGLE FORMED IN BRACKET - 0.20 SLOT

| WIRE SIZE | DEV. ANGLE | 1° | 2° | 3° | 5° | 7° | 8° | 9° | 10° | 11° | 12° | 14° | 15° | 17° | 20° | 22° | 25° | 27° | 30° |
|---|---|---|---|---|---|---|---|---|---|---|---|---|---|---|---|---|---|---|---|
| 014 x 014 | N/E | - | - | - | - | - | - | - | - | - | - | - | - | - | - | - | - | - | - |
| 014 x 018 | 23.4145 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.58 | 3.58 | 6.58 |
| 014 x 022 | 17.6109 | 0.00 | 0.00 | 0.00 | 0.00 | 0.00 | 0.00 | 0.00 | 0.00 | 0.00 | 0.00 | 0.00 | 0.00 | 0.00 | 2.39 | 4.39 | 7.39 | 9.39 | 12.39 |
| 014 x 025 | 15.0183 | 0.00 | 0.00 | 0.00 | 0.00 | 0.00 | 0.00 | 0.00 | 0.00 | 0.00 | 0.00 | 0.00 | 0.00 | 1.98 | 4.98 | 6.98 | 9.98 | 11.98 | 14.98 |
| 014 x 028 | 13.143 | 0.00 | 0.00 | 0.00 | 0.00 | 0.00 | 0.00 | 0.00 | 0.00 | 0.00 | 0.00 | 0.85 | 1.85 | 3.85 | 6.85 | 8.85 | 11.85 | 13.85 | 16.85 |
| 015 x 015 | 25.5288 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.47 | 4.47 |
| 015 x 018 | 18.7976 | 0.00 | 0.00 | 0.00 | 0.00 | 0.00 | 0.00 | 0.00 | 0.00 | 0.00 | 0.00 | 0.00 | 0.00 | 0.00 | 1.20 | 3.20 | 6.20 | 8.20 | 11.20 |
| 015 x 022 | 14.4002 | 0.00 | 0.00 | 0.00 | 0.00 | 0.00 | 0.00 | 0.00 | 0.00 | 0.00 | 0.00 | 0.00 | 0.60 | 2.60 | 5.60 | 7.60 | 10.60 | 12.60 | 15.60 |
| 015 x 025 | 12.3501 | 0.00 | 0.00 | 0.00 | 0.00 | 0.00 | 0.00 | 0.00 | 0.00 | 0.00 | 0.00 | 1.65 | 2.65 | 4.65 | 7.65 | 9.65 | 12.65 | 14.65 | 17.65 |
| 015 x 028 | 10.8441 | 0.00 | 0.00 | 0.00 | 0.00 | 0.00 | 0.00 | 0.00 | 0.00 | 0.15 | 1.15 | 3.15 | 4.15 | 6.15 | 9.15 | 11.15 | 14.15 | 16.15 | 19.15 |
| 016 x 018 | 14.5119 | 0.00 | 0.00 | 0.00 | 0.00 | 0.00 | 0.00 | 0.00 | 0.00 | 0.00 | 0.00 | 0.00 | 0.49 | 2.49 | 5.49 | 7.49 | 10.49 | 12.49 | 15.49 |
| 016 x 016 | 17.1144 | 0.00 | 0.00 | 0.00 | 0.00 | 0.00 | 0.00 | 0.00 | 0.00 | 0.00 | 0.00 | 0.00 | 0.00 | 0.00 | 2.88 | 4.88 | 7.88 | 9.88 | 12.88 |
| 016 x 022 | 11.298 | 0.00 | 0.00 | 0.00 | 0.00 | 0.00 | 0.00 | 0.00 | 0.00 | 0.00 | 0.70 | 2.70 | 3.70 | 5.70 | 8.70 | 10.70 | 13.70 | 15.70 | 18.70 |
| 016 x 025 | 9.74312 | 0.00 | 0.00 | 0.00 | 0.00 | 0.00 | 0.00 | 0.00 | 0.25 | 1.25 | 2.25 | 4.25 | 5.25 | 7.25 | 10.25 | 12.25 | 15.25 | 17.25 | 20.25 |
| 016 x 028 | 8.58394 | 0.00 | 0.00 | 0.00 | 0.00 | 0.00 | 0.00 | 0.41 | 1.41 | 2.41 | 3.41 | 5.41 | 6.41 | 8.41 | 11.41 | 13.41 | 16.41 | 18.41 | 21.41 |
| 017 x 017 | 11.2934 | 0.00 | 0.00 | 0.00 | 0.00 | 0.00 | 0.00 | 0.00 | 0.00 | 0.00 | 0.70 | 2.70 | 3.70 | 5.70 | 8.70 | 10.70 | 13.70 | 15.70 | 18.70 |
| 017 x 022 | 8.3066 | 0.00 | 0.00 | 0.00 | 0.00 | 0.00 | 0.00 | 0.69 | 1.69 | 2.69 | 3.69 | 5.69 | 6.69 | 8.69 | 11.69 | 13.69 | 16.69 | 18.69 | 21.69 |
| 017 x 025 | 7.20182 | 0.00 | 0.00 | 0.00 | 0.00 | 0.00 | 0.80 | 1.80 | 2.80 | 3.80 | 4.80 | 6.80 | 7.80 | 9.80 | 12.80 | 14.80 | 17.80 | 19.80 | 22.80 |
| 017 x 028 | 6.36646 | 0.00 | 0.00 | 0.00 | 0.00 | 0.63 | 1.63 | 2.63 | 3.63 | 4.63 | 5.63 | 7.63 | 8.63 | 10.63 | 13.63 | 15.63 | 18.63 | 20.63 | 23.63 |
| 0175 x 0175 | 8.91285 | 0.00 | 0.00 | 0.00 | 0.00 | 0.00 | 0.00 | 0.08 | 1.08 | 2.08 | 3.08 | 5.08 | 6.08 | 8.08 | 11.08 | 13.08 | 16.08 | 18.08 | 21.08 |
| 0175 x 022 | 6.85281 | 0.00 | 0.00 | 0.00 | 0.00 | 0.14 | 1.14 | 2.14 | 3.14 | 4.14 | 5.14 | 7.14 | 8.14 | 10.14 | 13.14 | 15.14 | 18.14 | 20.14 | 23.14 |
| 0175 x 025 | 5.95687 | 0.00 | 0.00 | 0.00 | 0.00 | 1.04 | 2.04 | 3.04 | 4.04 | 5.04 | 6.04 | 8.04 | 9.04 | 11.04 | 14.04 | 16.04 | 19.04 | 21.04 | 24.04 |
| 0175 x 028 | 5.27479 | 0.00 | 0.00 | 0.00 | 0.00 | 1.72 | 2.72 | 3.72 | 4.72 | 5.72 | 6.72 | 8.72 | 9.72 | 11.72 | 14.72 | 16.72 | 19.72 | 21.72 | 24.72 |
| 018 x 018 | 6.78308 | 0.00 | 0.00 | 0.00 | 0.00 | 0.21 | 1.21 | 2.21 | 3.21 | 4.21 | 5.21 | 7.21 | 8.21 | 10.21 | 13.21 | 15.21 | 18.21 | 20.21 | 23.21 |
| 018 x 022 | 5.42695 | 0.00 | 0.00 | 0.00 | 0.00 | 1.57 | 2.57 | 3.57 | 4.57 | 5.57 | 6.57 | 8.57 | 9.57 | 11.57 | 14.57 | 16.57 | 19.57 | 21.57 | 24.57 |
| 018 x 025 | 4.72449 | 0.00 | 0.00 | 0.00 | 0.27 | 2.27 | 3.27 | 4.27 | 5.27 | 6.27 | 7.27 | 9.27 | 10.27 | 12.27 | 15.27 | 17.27 | 20.27 | 22.27 | 25.27 |
| 018 x 028 | 4.19498 | 0.00 | 0.00 | 0.00 | 0.80 | 2.80 | 3.80 | 4.80 | 5.80 | 6.80 | 7.80 | 9.80 | 10.80 | 12.80 | 15.80 | 17.80 | 20.80 | 22.80 | 25.80 |
| 019 x 019 | 3.10098 | 0.00 | 0.00 | 0.00 | 1.90 | 3.90 | 4.90 | 5.90 | 6.90 | 7.90 | 8.90 | 10.90 | 11.90 | 13.90 | 16.90 | 18.90 | 21.90 | 23.90 | 26.90 |
| 019 x 025 | 2.32842 | 0.00 | 0.00 | 0.67 | 2.67 | 4.67 | 5.67 | 6.67 | 7.67 | 8.67 | 9.67 | 11.67 | 12.67 | 14.67 | 17.67 | 19.67 | 22.67 | 24.67 | 27.67 |
| 019 x 028 | 2.07215 | 0.00 | 0.00 | 0.93 | 2.93 | 4.93 | 5.93 | 6.93 | 7.93 | 8.93 | 9.93 | 11.93 | 12.93 | 14.93 | 17.93 | 19.93 | 22.93 | 24.93 | 27.93 |
| 0195 x 0195 | 1.48863 | 0.00 | 0.51 | 1.51 | 3.51 | 5.51 | 6.51 | 7.51 | 8.51 | 9.51 | 10.51 | 12.51 | 13.51 | 15.51 | 18.51 | 20.51 | 23.51 | 25.51 | 28.51 |
| 0195 x 025 | 1.11508 | 0.00 | 0.84 | 1.84 | 3.84 | 5.84 | 6.84 | 7.84 | 8.84 | 9.84 | 10.84 | 12.84 | 13.84 | 15.84 | 18.84 | 20.84 | 23.84 | 25.84 | 28.84 |
| 0195 x 028 | 1.02964 | 0.00 | 0.97 | 1.97 | 3.97 | 5.97 | 6.97 | 7.97 | 8.97 | 9.97 | 10.97 | 12.97 | 13.97 | 15.97 | 18.97 | 20.97 | 23.97 | 25.97 | 28.97 |

FIG. 8

TORQUE ANGLE FORMED IN BRACKET - .018 SLOT

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 014 x 014 | 20.3864 | 0.00 | 0.00 | 0.00 | 0.00 | 0.00 | 0.00 | 0.00 | 0.00 | 0.00 | 0.00 | 0.00 | 0.00 | 0.00 | 1.61 | 4.61 | 6.61 | 9.61 |
| 014 x 018 | 14.25 | 0.00 | 0.00 | 0.00 | 0.00 | 0.00 | 0.00 | 0.00 | 0.00 | 0.00 | 0.00 | 0.00 | 0.75 | 2.75 | 7.75 | 10.75 | 12.75 | 15.75 |
| 014 x 022 | 11.1802 | 0.00 | 0.00 | 0.00 | 0.00 | 0.00 | 0.00 | 0.00 | 0.00 | 0.00 | 0.81 | 2.81 | 3.81 | 5.81 | 10.81 | 13.81 | 15.81 | 18.81 |
| 014 x 025 | 9.66844 | 0.00 | 0.00 | 0.00 | 0.00 | 0.00 | 0.00 | 0.00 | 0.33 | 1.33 | 2.33 | 4.33 | 5.33 | 7.33 | 12.33 | 15.33 | 17.33 | 20.33 |
| 014 x 028 | 8.5338 | 0.00 | 0.00 | 0.00 | 0.00 | 0.00 | 0.00 | 0.46 | 1.46 | 2.46 | 3.46 | 5.46 | 6.46 | 8.46 | 13.46 | 16.46 | 18.46 | 21.46 |
| 015 x 015 | 13.0519 | 0.00 | 0.00 | 0.00 | 0.00 | 0.00 | 0.00 | 0.00 | 0.00 | 0.00 | 0.00 | 0.95 | 1.95 | 3.95 | 8.95 | 11.95 | 13.95 | 16.95 |
| 015 x 018 | 10.3889 | 0.00 | 0.00 | 0.00 | 0.00 | 0.00 | 0.00 | 0.00 | 0.00 | 0.61 | 1.61 | 3.61 | 4.61 | 6.61 | 11.61 | 14.61 | 16.61 | 19.61 |
| 015 x 022 | 8.2453 | 0.00 | 0.00 | 0.00 | 0.00 | 0.00 | 0.00 | 0.75 | 1.75 | 2.75 | 3.75 | 5.75 | 6.75 | 8.75 | 13.75 | 16.75 | 18.75 | 21.75 |
| 015 x 025 | 7.16329 | 0.00 | 0.00 | 0.00 | 0.00 | 0.00 | 0.84 | 1.84 | 2.84 | 3.84 | 4.84 | 6.84 | 7.84 | 9.84 | 14.84 | 17.84 | 19.84 | 22.84 |
| 015 x 028 | 6.33945 | 0.00 | 0.00 | 0.00 | 0.00 | 0.66 | 1.66 | 2.66 | 3.66 | 4.66 | 5.66 | 7.66 | 8.66 | 10.66 | 15.66 | 18.66 | 20.66 | 23.66 |
| 016 x 016 | 7.70205 | 0.00 | 0.00 | 0.00 | 0.00 | 0.00 | 0.30 | 1.30 | 2.30 | 3.30 | 4.30 | 6.30 | 7.30 | 9.30 | 14.30 | 17.30 | 19.30 | 22.30 |
| 016 x 018 | 6.73292 | 0.00 | 0.00 | 0.00 | 0.00 | 0.26 | 1.26 | 2.26 | 3.26 | 4.26 | 5.26 | 7.26 | 8.26 | 10.26 | 15.26 | 18.26 | 20.26 | 23.26 |
| 016 x 022 | 5.40176 | 0.00 | 0.00 | 0.00 | 0.00 | 1.60 | 2.60 | 3.60 | 4.60 | 5.60 | 6.60 | 8.60 | 9.60 | 11.60 | 16.60 | 19.60 | 21.60 | 24.60 |
| 016 x 025 | 4.71296 | 0.00 | 0.00 | 0.00 | 0.28 | 2.28 | 3.28 | 4.28 | 5.28 | 6.28 | 7.28 | 9.28 | 10.28 | 12.28 | 17.28 | 20.28 | 22.28 | 25.28 |
| 016 x 028 | 4.18351 | 0.00 | 0.00 | 0.00 | 0.81 | 2.81 | 3.81 | 4.81 | 5.81 | 6.81 | 7.81 | 9.81 | 10.81 | 12.81 | 17.81 | 20.81 | 22.81 | 25.81 |
| 017 x 017 | 3.47801 | 0.00 | 0.00 | 0.00 | 1.52 | 3.52 | 4.52 | 5.52 | 6.52 | 7.52 | 8.52 | 10.52 | 11.52 | 13.52 | 18.52 | 21.52 | 23.52 | 26.52 |
| 017 x 022 | 2.65275 | 0.00 | 0.00 | 0.34 | 2.34 | 4.34 | 5.34 | 6.34 | 7.34 | 8.34 | 9.34 | 11.34 | 12.34 | 14.34 | 19.34 | 22.34 | 24.34 | 27.34 |
| 017 x 025 | 2.32453 | 0.00 | 0.00 | 0.67 | 2.67 | 4.67 | 5.67 | 6.67 | 7.67 | 8.67 | 9.67 | 11.67 | 12.67 | 14.67 | 19.67 | 22.67 | 24.67 | 27.67 |
| 017 x 028 | 2.06942 | 0.00 | 0.00 | 0.93 | 2.93 | 4.93 | 5.93 | 6.93 | 7.93 | 8.93 | 9.93 | 11.93 | 12.93 | 14.93 | 19.93 | 22.93 | 24.93 | 27.93 |
| 0175 x 0175 | 1.66134 | 0.00 | 0.34 | 1.34 | 3.34 | 5.34 | 6.34 | 7.34 | 8.34 | 9.34 | 10.34 | 12.34 | 13.34 | 15.34 | 20.34 | 23.34 | 25.34 | 28.34 |
| 0175 x 022 | 1.31428 | 0.00 | 0.68 | 1.68 | 3.68 | 5.68 | 6.68 | 7.68 | 8.68 | 9.68 | 10.68 | 12.68 | 13.68 | 15.68 | 20.68 | 23.68 | 25.68 | 28.68 |
| 0175 x 025 | 1.15413 | 0.00 | 0.84 | 1.84 | 3.84 | 5.84 | 6.84 | 7.84 | 8.84 | 9.84 | 10.84 | 12.84 | 13.84 | 15.84 | 20.84 | 23.84 | 25.84 | 28.84 |
| 0175 x 028 | 1.02897 | 0.00 | 0.97 | 1.97 | 3.97 | 5.97 | 6.97 | 7.97 | 8.97 | 9.97 | 10.97 | 12.97 | 13.97 | 15.97 | 20.97 | 23.97 | 25.97 | 28.97 |

FIG. 9

TORQUE ANGLE FORMED IN BRACKET-.022 SLOT

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 016 x 016 | 31.4759 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 016 x 022 | 17.9453 | 0.00 | 0.00 | 0.00 | 0.00 | 0.00 | 0.00 | 0.00 | 0.00 | 0.00 | 0.00 | 0.00 | 0.00 | 0.00 | 4.05 | 7.05 | 9.05 | 12.05 |
| 016 x 025 | 15.2144 | 0.00 | 0.00 | 0.00 | 0.00 | 0.00 | 0.00 | 0.00 | 0.00 | 0.00 | 0.00 | 0.00 | 0.00 | 1.78 | 6.78 | 9.78 | 11.78 | 14.78 |
| 016 x 028 | 13.2702 | 0.00 | 0.00 | 0.00 | 0.00 | 0.00 | 0.00 | 0.00 | 0.00 | 0.00 | 0.00 | 0.73 | 1.73 | 3.73 | 8.73 | 11.73 | 13.73 | 16.73 |
| 017 x 017 | 21.217 | 0.00 | 0.00 | 0.00 | 0.00 | 0.00 | 0.00 | 0.00 | 0.00 | 0.00 | 0.00 | 0.00 | 0.00 | 0.00 | 0.78 | 3.78 | 5.78 | 8.78 |
| 017 x 022 | 14.6115 | 0.00 | 0.00 | 0.00 | 0.00 | 0.00 | 0.00 | 0.00 | 0.00 | 0.00 | 0.00 | 0.00 | 0.39 | 2.39 | 7.39 | 10.39 | 12.39 | 15.39 |
| 017 x 025 | 12.4778 | 0.00 | 0.00 | 0.00 | 0.00 | 0.00 | 0.00 | 0.00 | 0.00 | 0.00 | 0.00 | 1.52 | 2.52 | 4.52 | 9.52 | 12.52 | 14.52 | 17.52 |
| 017 x 028 | 10.9284 | 0.00 | 0.00 | 0.00 | 0.00 | 0.00 | 0.00 | 0.00 | 0.00 | 0.07 | 1.07 | 3.07 | 4.07 | 6.07 | 11.07 | 14.07 | 16.07 | 19.07 |
| 0175 x 0175 | 17.7396 | 0.00 | 0.00 | 0.00 | 0.00 | 0.00 | 0.00 | 0.00 | 0.00 | 0.00 | 0.00 | 0.00 | 0.00 | 0.00 | 4.26 | 7.26 | 9.26 | 12.26 |
| 0175 x 022 | 12.9987 | 0.00 | 0.00 | 0.00 | 0.00 | 0.00 | 0.00 | 0.00 | 0.00 | 0.00 | 0.00 | 1.00 | 2.00 | 4.00 | 9.00 | 12.00 | 14.00 | 17.00 |
| 0175 x 025 | 11.1388 | 0.00 | 0.00 | 0.00 | 0.00 | 0.00 | 0.00 | 0.00 | 0.00 | 0.00 | 0.86 | 2.86 | 3.86 | 5.86 | 10.86 | 13.86 | 15.86 | 18.86 |
| 0175 x 028 | 9.7755 | 0.00 | 0.00 | 0.00 | 0.00 | 0.00 | 0.00 | 0.00 | 0.22 | 1.22 | 2.22 | 4.22 | 5.22 | 7.22 | 12.22 | 15.22 | 17.22 | 20.22 |
| 018 x 018 | 14.7962 | 0.00 | 0.00 | 0.00 | 0.00 | 0.00 | 0.00 | 0.00 | 0.00 | 0.00 | 0.00 | 0.00 | 0.20 | 2.20 | 7.20 | 10.20 | 12.20 | 15.20 |
| 018 x 022 | 11.4212 | 0.00 | 0.00 | 0.00 | 0.00 | 0.00 | 0.00 | 0.00 | 0.18 | 1.18 | 0.58 | 2.58 | 3.58 | 5.58 | 10.58 | 13.58 | 15.58 | 18.58 |
| 018 x 025 | 9.81971 | 0.00 | 0.00 | 0.00 | 0.00 | 0.00 | 0.00 | 0.36 | 1.36 | 2.36 | 2.18 | 4.18 | 5.18 | 7.18 | 12.18 | 15.18 | 17.18 | 20.18 |
| 018 x 028 | 8.6353 | 0.00 | 0.00 | 0.00 | 0.00 | 0.00 | 0.00 | 0.00 | 1.04 | 1.04 | 3.36 | 5.36 | 6.36 | 8.36 | 13.36 | 16.36 | 18.36 | 21.36 |
| 019 x 019 | 9.96038 | 0.00 | 0.00 | 0.00 | 0.00 | 0.00 | 0.00 | 0.63 | 0.04 | 2.63 | 2.04 | 4.04 | 5.04 | 7.04 | 12.04 | 15.04 | 17.04 | 20.04 |
| 019 x 022 | 8.36983 | 0.00 | 0.00 | 0.00 | 0.00 | 0.00 | 0.00 | 1.75 | 1.63 | 3.75 | 3.63 | 5.63 | 6.63 | 8.63 | 13.63 | 16.63 | 18.63 | 21.63 |
| 019 x 025 | 7.24215 | 0.00 | 0.00 | 0.00 | 0.00 | 0.60 | 0.75 | 2.60 | 2.75 | 4.60 | 4.75 | 6.75 | 7.75 | 9.75 | 14.75 | 17.75 | 19.75 | 22.75 |
| 019 x 028 | 6.39394 | 0.00 | 0.00 | 0.00 | 0.00 | 1.01 | 1.60 | 1.08 | 3.60 | 3.08 | 5.60 | 7.60 | 8.60 | 10.60 | 15.60 | 18.60 | 20.60 | 23.60 |
| 0195 x 0195 | 7.91687 | 0.00 | 0.00 | 0.00 | 0.00 | 0.10 | 0.08 | 2.10 | 2.08 | 4.10 | 4.08 | 6.08 | 7.08 | 9.08 | 14.08 | 17.08 | 19.08 | 22.08 |
| 0195 x 022 | 6.89477 | 0.00 | 0.00 | 0.00 | 0.00 | 1.01 | 1.10 | 2.10 | 3.10 | 4.10 | 5.10 | 7.10 | 8.10 | 10.10 | 15.10 | 18.10 | 20.10 | 23.10 |
| 0195 x 025 | 5.98397 | 0.00 | 0.00 | 0.00 | 0.00 | 1.01 | 2.01 | 3.01 | 4.01 | 5.01 | 6.01 | 8.01 | 9.01 | 11.01 | 16.01 | 19.01 | 21.01 | 24.01 |
| 0195 x 028 | 5.29339 | 0.00 | 0.00 | 0.00 | 0.00 | 1.70 | 2.70 | 3.70 | 4.70 | 5.70 | 6.70 | 8.70 | 9.70 | 11.70 | 16.70 | 19.70 | 21.70 | 24.70 |
| 020 x 020 | 6.06118 | 0.00 | 0.00 | 0.00 | 0.00 | 0.94 | 1.94 | 2.94 | 3.94 | 4.94 | 5.94 | 7.94 | 8.94 | 10.94 | 15.94 | 18.94 | 20.94 | 23.94 |
| 0215 x 0215 | 1.34845 | 0.00 | 0.65 | 1.65 | 3.65 | 5.65 | 6.65 | 7.65 | 8.65 | 9.65 | 10.65 | 12.65 | 13.65 | 15.65 | 20.65 | 23.65 | 25.65 | 28.65 |
| 0215 x 028 | 1.03031 | 0.00 | 0.97 | 1.97 | 3.97 | 5.97 | 6.97 | 7.97 | 8.97 | 9.97 | 10.97 | 12.97 | 13.97 | 15.97 | 20.97 | 23.97 | 25.97 | 28.97 |
| 021 x 025 | 2.3323 | 0.00 | 0.00 | 0.67 | 2.67 | 4.67 | 5.67 | 6.67 | 7.67 | 8.67 | 9.67 | 11.67 | 12.67 | 14.67 | 19.67 | 22.67 | 24.67 | 27.67 |
| 021 x 028 | 2.0749 | 0.00 | 0.00 | 0.93 | 2.93 | 4.93 | 5.93 | 6.93 | 7.93 | 8.93 | 9.93 | 11.93 | 12.93 | 14.93 | 19.93 | 22.93 | 24.93 | 27.93 |

FLAT-BEVEL WIRE, HORIZONTAL BEVEL INDENTION r = .00375

Torque Angles Manufactured into .020 Slot Bracket

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 014 x 014 | N/E | - | - | - | - | - | - | - | - | - | - | - | - | - | - | - | - | - |
| 014 x 018 | N/E | - | - | - | - | - | - | - | - | - | - | - | - | - | - | - | - | - |
| 014 x 022 | 38.88 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 014 x 025 | 24.52 | 0.00 | 0.00 | 0.00 | 0.00 | 0.00 | 0.00 | 0.00 | 0.00 | 0.00 | 0.00 | 0.00 | 0.00 | 0.00 | 0.00 | 0.48 | 2.48 | 6.48 |
| 014 x 028 | 19.34 | 0.00 | 0.00 | 0.00 | 0.00 | 0.00 | 0.00 | 0.00 | 0.00 | 0.00 | 0.00 | 0.00 | 0.00 | 0.00 | 2.66 | 5.66 | 7.66 | 10.66 |
| 015 x 015 | N/E | - | - | - | - | - | - | - | - | - | - | - | - | - | - | - | - | - |
| 015 x 018 | N/E | - | - | - | - | - | - | - | - | - | - | - | - | - | - | - | - | - |
| 015 x 022 | 27.50 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 2.50 |
| 015 x 025 | 19.59 | 0.00 | 0.00 | 0.00 | 0.00 | 0.00 | 0.00 | 0.00 | 0.00 | 0.00 | 0.00 | 0.00 | 0.00 | 0.00 | 2.41 | 5.41 | 7.41 | 10.41 |
| 015 x 028 | 15.75 | 0.00 | 0.00 | 0.00 | 0.00 | 0.00 | 0.00 | 0.00 | 0.00 | 0.00 | 0.00 | 0.00 | 0.00 | 1.25 | 6.25 | 9.25 | 11.25 | 14.25 |
| 016 x 016 | N/E | - | - | - | - | - | - | - | - | - | - | - | - | - | - | - | - | - |
| 016 x 018 | N/E | - | - | - | - | - | - | - | - | - | - | - | - | - | - | - | - | - |
| 016 x 020 | 28.07 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.93 |
| 016 x 025 | 15.07 | 0.00 | 0.00 | 0.00 | 0.00 | 0.00 | 0.00 | 0.00 | 0.00 | 0.00 | 0.00 | 0.00 | 0.00 | 0.00 | 1.96 | 4.96 | 6.96 | 9.96 |
| 016 x 028 | 12.30 | 0.00 | 0.00 | 0.00 | 0.00 | 0.00 | 0.00 | 0.00 | 0.00 | 0.00 | 0.00 | 1.70 | 2.70 | 4.70 | 9.70 | 12.70 | 14.70 | 17.70 |
| 017 x 017 | N/E | - | - | - | - | - | - | - | - | - | - | - | - | - | - | - | - | - |
| 017 x 020 | 17.74 | 0.00 | 0.00 | 0.00 | 0.00 | 0.00 | 0.00 | 0.00 | 0.00 | 0.00 | 0.00 | 0.00 | 0.00 | 0.00 | 4.26 | 7.26 | 9.26 | 12.26 |
| 017 x 022 | 13.98 | 0.00 | 0.00 | 0.00 | 0.00 | 0.00 | 0.00 | 0.00 | 0.00 | 0.00 | 0.00 | 0.02 | 1.02 | 3.02 | 8.02 | 11.02 | 13.02 | 16.02 |
| 017 x 025 | 10.89 | 0.00 | 0.00 | 0.00 | 0.00 | 0.00 | 0.00 | 0.00 | 0.11 | 1.11 | 3.11 | 4.11 | 6.11 | 11.11 | 14.11 | 16.11 | 19.11 | 18.70 |
| 017 x 028 | 9.01 | 0.00 | 0.00 | 0.00 | 0.00 | 0.00 | 0.00 | 0.00 | 0.99 | 1.99 | 2.99 | 4.99 | 5.99 | 7.99 | 12.99 | 15.99 | 17.99 | 20.99 |
| 0175 x 0175 | 22.62 | 0.00 | 0.00 | 0.00 | 0.00 | 0.00 | 0.00 | 0.00 | 0.00 | 0.00 | 0.00 | 0.00 | 0.00 | 0.00 | 0.00 | 2.38 | 4.38 | 7.38 |
| 0175 x 020 | 13.97 | 0.00 | 0.00 | 0.00 | 0.00 | 0.00 | 0.00 | 0.00 | 0.00 | 0.00 | 0.00 | 0.03 | 1.03 | 3.03 | 8.03 | 11.03 | 13.03 | 16.03 |
| 0175 x 022 | 11.29 | 0.00 | 0.00 | 0.00 | 0.00 | 0.00 | 0.00 | 0.00 | 0.00 | 0.00 | 0.71 | 2.71 | 3.71 | 5.71 | 10.71 | 13.71 | 15.71 | 18.71 |
| 0175 x 025 | 8.91 | 0.00 | 0.00 | 0.00 | 0.00 | 0.00 | 0.00 | 0.09 | 1.09 | 2.09 | 3.09 | 5.09 | 6.09 | 8.09 | 13.09 | 16.09 | 18.09 | 21.09 |
| 0175 x 028 | 7.42 | 0.00 | 0.00 | 0.00 | 0.00 | 0.00 | 0.58 | 1.58 | 2.58 | 3.58 | 4.58 | 6.58 | 7.58 | 9.58 | 14.58 | 17.58 | 19.58 | 22.58 |
| 018 x 018 | 13.95 | 0.00 | 0.00 | 0.00 | 0.00 | 0.00 | 0.00 | 0.00 | 0.00 | 0.00 | 0.00 | 0.05 | 1.05 | 3.05 | 8.05 | 11.05 | 13.05 | 16.05 |
| 018 x 020 | 10.65 | 0.00 | 0.00 | 0.00 | 0.00 | 0.00 | 0.00 | 0.00 | 1.23 | 0.35 | 1.35 | 3.35 | 4.35 | 6.35 | 11.35 | 14.35 | 16.35 | 19.35 |
| 018 x 022 | 8.77 | 0.00 | 0.00 | 0.00 | 0.00 | 0.00 | 0.00 | 0.23 | 1.23 | 2.23 | 3.23 | 5.23 | 6.23 | 8.23 | 13.23 | 16.23 | 18.23 | 21.23 |
| 018 x 025 | 7.01 | 0.00 | 0.00 | 0.00 | 0.00 | 0.00 | 0.99 | 1.99 | 2.99 | 3.99 | 4.99 | 6.99 | 7.99 | 9.99 | 14.99 | 17.99 | 19.99 | 22.99 |
| 018 x 028 | 5.86 | 0.00 | 0.00 | 0.00 | 0.00 | 1.14 | 2.14 | 3.14 | 4.14 | 5.14 | 6.14 | 8.14 | 9.14 | 11.14 | 16.14 | 19.14 | 21.14 | 24.14 |
| 019 x 019 | 5.41 | 0.00 | 0.00 | 0.00 | 0.85 | 1.59 | 2.59 | 3.59 | 4.59 | 5.59 | 6.59 | 8.89 | 9.59 | 11.59 | 16.59 | 19.59 | 21.59 | 24.59 |
| 019 x 022 | 4.15 | 0.00 | 0.00 | 0.00 | 1.62 | 2.85 | 3.85 | 4.85 | 5.85 | 6.85 | 7.85 | 9.85 | 10.85 | 12.85 | 17.85 | 20.85 | 22.85 | 25.85 |
| 019 x 025 | 3.38 | 0.00 | 0.00 | 0.14 | 2.14 | 3.62 | 4.62 | 5.62 | 6.62 | 7.62 | 8.62 | 10.62 | 11.62 | 13.62 | 18.62 | 21.62 | 23.62 | 26.62 |
| 019 x 028 | 2.86 | 0.00 | 0.00 | 0.14 | 2.14 | 4.14 | 5.14 | 6.14 | 7.14 | 8.14 | 9.14 | 11.14 | 12.14 | 14.14 | 19.14 | 22.14 | 24.14 | 27.14 |

FIG. 12

FLAT-BEVEL WIRE, HORIZONTAL BEVEL INDENTATION r=.00375
Torque Angles Manufactured into .018 Slot Bracket

| WIRE SIZE | ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 014 x 014 | N/E | -- | -- | -- | -- | -- | -- | -- | -- | -- | -- | -- | -- | -- | -- | -- | -- | -- |
| 014 x 018 | N/E | -- | -- | -- | -- | -- | -- | -- | -- | -- | -- | -- | -- | -- | -- | -- | -- | -- |
| 014 x 022 | 19.26 | 0.00 | 0.00 | 0.00 | 0.00 | 0.00 | 0.00 | 0.00 | 0.00 | 0.00 | 0.00 | 0.00 | 0.00 | 0.00 | 2.74 | 5.74 | 7.74 | 10.74 |
| 014 x 025 | 14.77 | 0.00 | 0.00 | 0.00 | 0.00 | 0.00 | 0.00 | 0.00 | 0.00 | 0.00 | 0.00 | 0.00 | 0.23 | 2.23 | 7.23 | 10.23 | 12.23 | 15.23 |
| 014 x 028 | 12.15 | 0.00 | 0.00 | 0.00 | 0.00 | 0.00 | 0.00 | 0.00 | 0.00 | 0.00 | 0.00 | 1.85 | 2.85 | 4.85 | 9.85 | 12.85 | 14.85 | 17.85 |
| 015 x 015 | N/E | -- | -- | -- | -- | -- | -- | -- | -- | -- | -- | -- | -- | -- | -- | -- | -- | -- |
| 015 x 018 | 24.44 | 0.00 | 0.00 | 0.00 | 0.00 | 0.00 | 0.00 | 0.00 | 0.00 | 0.00 | 0.00 | 0.00 | 0.00 | 0.00 | 0.00 | 0.56 | 2.56 | 5.56 |
| 015 x 022 | 13.66 | 0.00 | 0.00 | 0.00 | 0.00 | 0.00 | 0.00 | 0.00 | 0.00 | 0.00 | 0.00 | 0.34 | 1.34 | 3.34 | 8.34 | 11.34 | 13.34 | 16.34 |
| 015 x 025 | 10.75 | 0.00 | 0.00 | 0.00 | 0.00 | 0.00 | 0.00 | 0.00 | 0.00 | 0.25 | 1.25 | 3.25 | 4.25 | 5.25 | 11.25 | 14.25 | 16.25 | 18.25 |
| 015 x 028 | 8.93 | 0.00 | 0.00 | 0.00 | 0.00 | 0.00 | 0.00 | 0.07 | 1.07 | 2.07 | 3.07 | 5.07 | 6.07 | 8.07 | 13.07 | 15.07 | 18.07 | 21.07 |
| 016 x 016 | 21.45 | 0.00 | 0.00 | 0.00 | 0.00 | 0.00 | 0.00 | 0.00 | 0.00 | 0.00 | 0.00 | 0.00 | 0.00 | 0.00 | 0.55 | 3.55 | 5.55 | 8.55 |
| 016 x 018 | 13.42 | 0.00 | 0.00 | 0.00 | 0.00 | 0.00 | 0.00 | 0.00 | 0.00 | 0.00 | 0.00 | 0.58 | 1.58 | 3.58 | 8.58 | 11.58 | 13.58 | 18.58 |
| 016 x 020 | 10.44 | 0.00 | 0.00 | 0.00 | 0.00 | 0.00 | 0.00 | 0.34 | 1.34 | 0.56 | 1.56 | 3.56 | 4.56 | 6.56 | 11.56 | 14.56 | 16.56 | 19.56 |
| 016 x 022 | 8.66 | 0.00 | 0.00 | 0.00 | 0.00 | 0.00 | 0.00 | 2.05 | 3.05 | 2.34 | 3.34 | 5.34 | 6.34 | 8.34 | 13.34 | 16.34 | 18.34 | 21.34 |
| 016 x 025 | 6.95 | 0.00 | 0.00 | 0.00 | 0.00 | 0.05 | 1.05 | 3.17 | 4.17 | 4.05 | 5.05 | 7.05 | 8.05 | 10.05 | 15.05 | 18.05 | 20.05 | 23.05 |
| 016 x 028 | 5.83 | 0.00 | 0.00 | 0.00 | 0.00 | 1.17 | 2.17 | 2.24 | 3.24 | 5.17 | 6.17 | 8.17 | 9.17 | 11.17 | 16.17 | 18.17 | 21.17 | 24.17 |
| 017 x 017 | 6.76 | 0.00 | 0.00 | 0.00 | 0.13 | 0.24 | 1.24 | 4.13 | 5.13 | 4.24 | 5.24 | 7.24 | 8.24 | 10.24 | 15.24 | 18.24 | 20.24 | 23.24 |
| 017 x 020 | 4.87 | 0.00 | 0.00 | 0.00 | 0.67 | 2.12 | 3.13 | 4.67 | 5.67 | 6.13 | 7.13 | 9.13 | 10.13 | 12.13 | 17.13 | 20.13 | 22.13 | 26.13 |
| 017 x 022 | 4.13 | 0.00 | 0.00 | 0.14 | 1.63 | 2.67 | 3.67 | 5.63 | 6.63 | 6.67 | 7.67 | 9.67 | 10.67 | 12.67 | 17.67 | 20.67 | 22.37 | 25.37 |
| 017 x 025 | 3.37 | 0.00 | 0.00 | 0.00 | 2.14 | 3.63 | 4.63 | 6.14 | 7.14 | 7.63 | 8.63 | 10.63 | 11.63 | 13.63 | 18.63 | 21.63 | 23.63 | 26.63 |
| 017 x 028 | 2.86 | 0.00 | 0.00 | 0.00 | 2.00 | 4.14 | 5.14 | 6.00 | 7.00 | 8.14 | 9.14 | 11.14 | 12.14 | 14.14 | 18.14 | 22.14 | 24.14 | 27.14 |
| 0175 x 0175 | 3.00 | 0.00 | 0.00 | 0.00 | 2.00 | 4.00 | 5.00 | 6.00 | 7.00 | 8.00 | 9.00 | 11.00 | 12.00 | 14.00 | 18.00 | 22.00 | 24.00 | 27.00 |
| 0175 x 020 | 2.36 | 0.00 | 0.00 | 0.64 | 2.64 | 4.64 | 5.64 | 6.64 | 7.64 | 8.64 | 9.64 | 11.64 | 12.64 | 14.64 | 19.64 | 22.64 | 24.64 | 27.64 |
| 0175 x 022 | 2.02 | 0.00 | 0.00 | 0.96 | 2.96 | 4.96 | 5.96 | 6.96 | 7.96 | 8.96 | 9.96 | 11.96 | 12.96 | 14.96 | 19.96 | 22.96 | 24.96 | 27.96 |
| 0175 x 025 | 1.66 | 0.00 | 0.34 | 1.34 | 3.34 | 5.34 | 6.34 | 7.34 | 8.34 | 9.34 | 10.34 | 12.34 | 13.34 | 15.34 | 20.34 | 23.34 | 25.34 | 28.34 |
| 0175 x 028 | 1.41 | 0.00 | 0.59 | 1.59 | 3.59 | 5.59 | 6.59 | 7.59 | 8.59 | 9.59 | 10.59 | 12.59 | 13.59 | 15.59 | 20.59 | 23.59 | 25.59 | 28.59 |

FLAT-BEVEL WIRE, HORIZONTAL BEVEL INDENTATION r=.00375
Torque Angles Manufactured into .022 Slot Bracket

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 016 x 016 | N/E | -- | -- | -- | -- | -- | -- | -- | -- | -- | -- | -- | -- | -- | -- | -- | -- | -- |
| 016 x 018 | N/E | -- | -- | -- | -- | -- | -- | -- | -- | -- | -- | -- | -- | -- | -- | -- | -- | -- |
| 016 x 020 | N/E | -- | -- | -- | -- | -- | -- | -- | -- | -- | -- | -- | -- | -- | -- | -- | -- | -- |
| 016 x 022 | N/E | -- | -- | -- | -- | -- | -- | -- | -- | -- | -- | -- | -- | -- | -- | -- | -- | -- |
| 016 x 025 | 25.66 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.34 | 4.34 |
| 016 x 028 | 19.81 | 0.00 | 0.00 | 0.00 | 0.00 | 0.00 | 0.00 | 0.00 | 0.00 | 0.00 | 0.00 | 0.00 | 0.00 | 0.00 | 2.19 | 5.19 | 7.19 | 10.19 |
| 017 x 017 | N/E | -- | -- | -- | -- | -- | -- | -- | -- | -- | -- | -- | -- | -- | -- | -- | -- | -- |
| 017 x 020 | N/E | -- | -- | -- | -- | -- | -- | -- | -- | -- | -- | -- | -- | -- | -- | -- | -- | -- |
| 017 x 022 | 30.40 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 017 x 025 | 20.22 | 0.00 | 0.00 | 0.00 | 0.00 | 0.00 | 0.00 | 0.00 | 0.00 | 0.00 | 0.00 | 0.00 | 0.00 | 0.00 | 1.78 | 4.78 | 8.78 | 9.78 |
| 017 x 028 | 16.03 | 0.00 | 0.00 | 0.00 | 0.00 | 0.00 | 0.00 | 0.00 | 0.00 | 0.00 | 0.00 | 0.00 | 0.00 | 0.97 | 5.97 | 8.97 | 10.97 | 13.97 |
| 0175 x 0175 | N/E | -- | -- | -- | -- | -- | -- | -- | -- | -- | -- | -- | -- | -- | -- | -- | -- | -- |
| 0175 x 020 | N/E | -- | -- | -- | -- | -- | -- | -- | -- | -- | -- | -- | -- | -- | -- | -- | -- | -- |
| 0175 x 022 | 25.12 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.66 | 4.66 |
| 0175 x 025 | 17.74 | 0.00 | 0.00 | 0.00 | 0.00 | 0.00 | 0.00 | 0.00 | 0.00 | 0.00 | 0.00 | 0.00 | 0.00 | 0.00 | 4.26 | 7.26 | 9.26 | 12.26 |
| 0175 x 028 | 14.22 | 0.00 | 0.00 | 0.00 | 0.00 | 0.00 | 0.00 | 0.00 | 0.00 | 0.00 | 0.00 | 1.54 | 2.54 | 4.54 | 7.78 | 10.78 | 12.78 | 15.78 |
| 018 x 018 | N/E | -- | -- | -- | -- | -- | -- | -- | -- | -- | -- | -- | -- | -- | -- | -- | -- | -- |
| 018 x 020 | N/E | -- | -- | -- | -- | -- | -- | -- | -- | -- | -- | -- | -- | -- | -- | -- | -- | -- |
| 018 x 022 | 20.99 | 0.00 | 0.00 | 0.00 | 0.00 | 0.00 | 0.00 | 0.00 | 0.00 | 0.00 | 0.00 | 0.00 | 0.00 | 0.00 | 1.01 | 4.01 | 6.01 | 9.01 |
| 018 x 025 | 15.40 | 0.00 | 0.00 | 0.00 | 0.00 | 0.00 | 0.00 | 0.00 | 0.00 | 0.00 | 0.00 | 0.00 | 0.00 | 1.60 | 6.60 | 8.80 | 11.60 | 14.60 |
| 018 x 028 | 12.46 | 0.00 | 0.00 | 0.00 | 0.00 | 0.00 | 0.00 | 0.00 | 0.00 | 0.00 | 0.00 | 1.54 | 2.54 | 4.54 | 9.54 | 12.54 | 14.54 | 17.54 |
| 019 x 019 | 23.31 | 0.00 | 0.00 | 0.00 | 0.00 | 0.00 | 0.00 | 0.00 | 0.00 | 0.00 | 0.00 | 0.00 | 0.00 | 0.00 | 0.00 | 1.69 | 3.69 | 6.69 |
| 019 x 022 | 14.34 | 0.00 | 0.00 | 0.00 | 0.00 | 0.00 | 0.00 | 0.00 | 0.00 | 0.00 | 0.00 | 2.96 | 3.96 | 2.86 | 7.86 | 10.86 | 12.86 | 15.86 |
| 019 x 025 | 11.04 | 0.00 | 0.00 | 0.00 | 0.00 | 0.00 | 0.00 | 1.53 | 2.53 | 3.53 | 4.53 | 4.91 | 5.91 | 5.96 | 10.96 | 13.96 | 15.96 | 18.96 |
| 019 x 028 | 9.09 | 0.00 | 0.00 | 0.00 | 0.00 | 0.00 | 0.00 | 5.60 | 6.60 | 7.60 | 8.60 | 2.50 | 3.50 | 7.91 | 12.91 | 15.91 | 17.81 | 20.91 |
| 0195 x 0195 | 15.52 | 0.00 | 0.00 | 0.00 | 0.00 | 0.00 | 0.00 | 0.00 | 0.00 | 0.00 | 0.00 | 0.00 | 0.00 | 1.46 | 6.46 | 9.46 | 11.46 | 14.46 |
| 0195 x 022 | 11.50 | 0.00 | 0.00 | 0.00 | 0.00 | 0.00 | 0.00 | 0.00 | 0.00 | 0.00 | 0.50 | 2.50 | 3.50 | 5.50 | 10.50 | 13.50 | 15.50 | 18.50 |
| 0195 x 025 | 9.01 | 0.00 | 0.00 | 0.00 | 0.00 | 0.00 | 0.00 | 0.99 | 1.99 | 2.99 | 4.53 | 4.99 | 5.99 | 7.99 | 12.99 | 15.99 | 17.99 | 20.99 |
| 0195 x 028 | 7.47 | 0.00 | 0.00 | 0.00 | 0.00 | 0.00 | 0.53 | 1.53 | 2.53 | 3.53 | 1.12 | 6.53 | 7.53 | 9.53 | 14.53 | 17.53 | 19.53 | 22.53 |
| 02 x 02 | 10.88 | 0.00 | 0.00 | 0.00 | 0.00 | 0.00 | 0.00 | 0.00 | 0.00 | 0.12 | 8.60 | 3.12 | 4.12 | 6.12 | 11.12 | 14.12 | 18.12 | 19.12 |
| 021 x 025 | 3.40 | 0.00 | 0.00 | 0.00 | 1.60 | 3.60 | 4.60 | 5.60 | 6.60 | 7.60 | 9.13 | 10.60 | 11.60 | 13.60 | 18.60 | 21.60 | 23.60 | 26.60 |
| 021 x 028 | 2.87 | 0.00 | 0.00 | 0.13 | 2.13 | 4.13 | 5.13 | 6.13 | 7.13 | 8.13 | 9.89 | 11.13 | 12.13 | 14.13 | 19.13 | 22.13 | 24.13 | 27.13 |
| 0215 x 0215 | 2.11 | 0.00 | 0.00 | 0.89 | 2.89 | 4.89 | 5.89 | 6.89 | 7.89 | 8.89 | 10.58 | 11.89 | 12.89 | 14.89 | 19.89 | 22.89 | 24.89 | 27.89 |
| 0215 x 028 | 1.42 | 0.00 | 0.56 | 1.56 | 3.58 | 5.58 | 6.58 | 7.58 | 8.58 | 9.58 | 10.58 | 12.58 | 13.58 | 15.56 | 20.56 | 23.56 | 25.58 | 28.58 |

FIG. 13

ROUND-BEVEL WIRE, RADIUS OF CURVATURE r=.00375
Torque Angles Manufactured into .020 Slot Bracket

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 014 x 014 | N/E | -- | -- | -- | -- | -- | -- | -- | -- | -- | -- | -- | -- | -- | -- | -- | -- | -- |
| 014 x 018 | N/E | -- | -- | -- | -- | -- | -- | -- | -- | -- | -- | -- | -- | -- | -- | -- | -- | -- |
| 014 x 022 | 27.73 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 2.27 |
| 014 x 025 | 21.66 | 0.00 | 0.00 | 0.00 | 0.00 | 0.00 | 0.00 | 0.00 | 0.00 | 0.00 | 0.00 | 0.00 | 0.00 | 0.00 | 0.34 | 3.34 | 5.34 | 8.34 |
| 014 x 028 | 17.95 | 0.00 | 0.00 | 0.00 | 0.00 | 0.00 | 0.00 | 0.00 | 0.00 | 0.00 | 0.00 | 0.00 | 0.00 | 0.00 | 4.05 | 7.05 | 9.05 | 12.05 |
| 015 x 015 | N/E | -- | -- | -- | -- | -- | -- | -- | -- | -- | -- | -- | -- | -- | -- | -- | -- | -- |
| 015 x 018 | 40.10 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 015 x 022 | 22.62 | 0.00 | 0.00 | 0.00 | 0.00 | 0.00 | 0.00 | 0.00 | 0.00 | 0.00 | 0.00 | 0.00 | 0.00 | 0.00 | 0.00 | 2.38 | 4.38 | 7.38 |
| 015 x 025 | 17.84 | 0.00 | 0.00 | 0.00 | 0.00 | 0.00 | 0.00 | 0.00 | 0.00 | 0.00 | 0.00 | 0.00 | 0.00 | 0.00 | 4.16 | 7.16 | 9.16 | 12.16 |
| 015 x 028 | 14.84 | 0.00 | 0.00 | 0.00 | 0.00 | 0.00 | 0.00 | 0.00 | 0.00 | 0.00 | 0.00 | 0.00 | 0.16 | 2.16 | 7.16 | 10.16 | 12.16 | 15.16 |
| 016 x 016 | N/E | -- | -- | -- | -- | -- | -- | -- | -- | -- | -- | -- | -- | -- | -- | -- | -- | -- |
| 016 x 018 | 28.72 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.28 |
| 016 x 020 | 21.57 | 0.00 | 0.00 | 0.00 | 0.00 | 0.00 | 0.00 | 0.00 | 0.00 | 0.00 | 0.00 | 0.00 | 0.00 | 0.00 | 0.43 | 3.43 | 5.43 | 8.43 |
| 016 x 022 | 17.67 | 0.00 | 0.00 | 0.00 | 0.00 | 0.00 | 0.00 | 0.00 | 0.00 | 0.00 | 0.00 | 0.00 | 0.00 | 0.00 | 4.33 | 7.33 | 9.33 | 12.33 |
| 016 x 025 | 14.07 | 0.00 | 0.00 | 0.00 | 0.00 | 0.00 | 0.00 | 0.00 | 0.00 | 0.00 | 0.00 | 0.00 | 0.93 | 2.93 | 7.93 | 10.93 | 12.93 | 15.93 |
| 016 x 028 | 11.76 | 0.00 | 0.00 | 0.00 | 0.00 | 0.00 | 0.00 | 0.27 | 1.27 | 2.27 | 3.27 | 5.27 | 6.27 | 8.27 | 13.27 | 16.27 | 18.27 | 21.27 |
| 017 x 017 | 23.50 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 017 x 020 | 15.53 | 0.00 | 0.00 | 0.00 | 0.00 | 0.00 | 0.00 | 0.00 | 0.00 | 0.00 | 0.24 | 2.24 | 3.24 | 5.24 | 10.24 | 13.24 | 15.24 | 18.24 |
| 017 x 022 | 12.91 | 0.00 | 0.00 | 0.00 | 0.00 | 0.00 | 0.00 | 0.00 | 0.00 | 0.00 | 0.00 | 0.00 | 0.00 | 0.00 | 0.00 | 1.50 | 3.50 | 6.50 |
| 017 x 025 | 10.39 | 0.00 | 0.00 | 0.00 | 0.00 | 0.00 | 0.00 | 0.00 | 0.00 | 0.00 | 0.00 | 0.00 | 0.00 | 1.47 | 6.47 | 9.47 | 11.47 | 14.47 |
| 017 x 028 | 8.73 | 0.00 | 0.00 | 0.00 | 0.00 | 0.00 | 0.00 | 0.00 | 0.00 | 0.61 | 1.61 | 3.61 | 4.61 | 4.09 | 9.09 | 12.09 | 14.09 | 17.09 |
| 0175 x 0175 | 17.11 | 0.00 | 0.00 | 0.00 | 0.00 | 0.00 | 0.00 | 0.00 | 0.00 | 2.27 | 3.27 | 5.27 | 6.27 | 8.61 | 11.61 | 14.61 | 16.61 | 19.61 |
| 0175 x 020 | 12.68 | 0.00 | 0.00 | 0.00 | 0.00 | 0.00 | 0.00 | 0.00 | 0.00 | 0.00 | 0.00 | 0.00 | 0.00 | 0.00 | 13.27 | 16.27 | 18.27 | 21.27 |
| 0175 x 022 | 10.62 | 0.00 | 0.00 | 0.00 | 0.00 | 0.00 | 0.00 | 0.00 | 0.00 | 0.00 | 0.00 | 1.32 | 2.32 | 4.32 | 9.32 | 12.32 | 14.32 | 17.32 |
| 0175 x 025 | 8.58 | 0.00 | 0.00 | 0.00 | 0.00 | 0.00 | 0.00 | 0.00 | 0.00 | 0.36 | 1.36 | 3.36 | 4.36 | 6.36 | 11.36 | 14.36 | 16.36 | 19.36 |
| 0175 x 028 | 7.23 | 0.00 | 0.00 | 0.00 | 0.00 | 0.00 | 0.00 | 0.42 | 1.42 | 2.42 | 3.42 | 5.42 | 6.42 | 8.42 | 13.42 | 16.42 | 18.42 | 21.42 |
| 018 x 018 | 12.33 | 0.00 | 0.00 | 0.00 | 0.00 | 0.00 | 0.77 | 1.77 | 2.77 | 3.77 | 4.77 | 6.77 | 7.77 | 9.77 | 14.77 | 17.77 | 19.77 | 22.77 |
| 018 x 020 | 9.94 | 0.00 | 0.00 | 0.00 | 0.00 | 0.00 | 0.00 | 0.00 | 0.00 | 0.00 | 0.00 | 1.67 | 2.67 | 4.67 | 9.67 | 12.67 | 14.67 | 17.67 |
| 018 x 022 | 8.38 | 0.00 | 0.00 | 0.00 | 0.00 | 0.00 | 0.00 | 0.00 | 0.06 | 1.06 | 2.06 | 4.08 | 5.06 | 7.06 | 12.06 | 15.06 | 17.06 | 20.06 |
| 018 x 025 | 6.81 | 0.00 | 0.00 | 0.00 | 0.00 | 0.00 | 0.00 | 0.62 | 1.62 | 2.62 | 3.62 | 5.62 | 6.62 | 8.62 | 13.62 | 16.62 | 18.62 | 21.62 |
| 018 x 028 | 5.75 | 0.00 | 0.00 | 0.00 | 0.00 | 0.19 | 1.19 | 2.19 | 3.19 | 4.19 | 5.19 | 7.19 | 8.19 | 10.19 | 15.19 | 18.19 | 20.19 | 23.19 |
| 019 x 019 | 5.23 | 0.00 | 0.00 | 0.00 | 0.00 | 1.25 | 2.25 | 3.25 | 4.25 | 5.25 | 6.25 | 8.25 | 9.25 | 11.25 | 16.25 | 19.25 | 21.25 | 24.25 |
| 019 x 022 | 4.07 | 0.00 | 0.00 | 0.00 | 0.93 | 1.77 | 2.77 | 3.77 | 4.77 | 5.77 | 6.77 | 8.77 | 9.77 | 11.77 | 16.77 | 19.77 | 21.77 | 24.77 |
| 019 x 025 | 3.34 | 0.00 | 0.00 | 0.00 | 1.66 | 2.93 | 3.93 | 4.93 | 5.93 | 6.93 | 7.93 | 9.93 | 10.93 | 12.93 | 17.93 | 20.93 | 22.93 | 25.93 |
| 019 x 028 | 2.84 | 0.00 | 0.00 | 0.16 | 2.16 | 3.66 | 4.66 | 5.66 | 6.66 | 7.66 | 8.66 | 10.66 | 11.66 | 13.66 | 18.66 | 21.66 | 23.66 | 26.66 |
|  |  |  |  |  |  | 4.16 | 5.16 | 6.16 | 7.16 | 8.16 | 9.16 | 11.16 | 12.16 | 14.16 | 19.16 | 22.16 | 24.16 | 27.16 |

FIG. 14

ROUND-BEVEL WIRE, RADIUS OF CURVATURE r=.00375
Torque Angles Manufactured into .018 Slot Bracket

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 014 x 014 | N/E | - | - | - | - | - | - | - | - | - | - | - | - | - | - | - | - | - |
| 014 x 018 | 26.48 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.52 | 3.52 |
| 014 x 022 | 17.21 | 0.00 | 0.00 | 0.00 | 0.00 | 0.00 | 0.00 | 0.00 | 0.00 | 0.00 | 0.00 | 0.00 | 0.00 | 0.00 | 4.79 | 7.79 | 9.79 | 12.76 |
| 014 x 025 | 13.85 | 0.00 | 0.00 | 0.00 | 0.00 | 0.00 | 0.00 | 0.00 | 0.00 | 0.00 | 0.00 | 0.15 | 1.15 | 3.15 | 6.15 | 11.15 | 13.15 | 15.15 |
| 014 x 028 | 11.63 | 0.00 | 0.00 | 0.00 | 0.00 | 0.00 | 0.00 | 0.00 | 0.00 | 0.00 | 0.00 | 2.37 | 3.37 | 5.37 | 10.37 | 13.37 | 15.37 | 18.37 |
| 015 x 015 | 36.87 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 015 x 018 | 18.92 | 0.00 | 0.00 | 0.00 | 0.00 | 0.00 | 0.00 | 0.00 | 0.00 | 0.00 | 0.00 | 0.00 | 0.00 | 0.00 | 3.06 | 6.08 | 8.06 | 11.08 |
| 015 x 022 | 12.68 | 0.00 | 0.00 | 0.00 | 0.00 | 0.00 | 0.00 | 0.00 | 0.00 | 0.00 | 0.00 | 1.32 | 2.32 | 4.32 | 9.32 | 12.32 | 14.32 | 17.32 |
| 015 x 025 | 10.27 | 0.00 | 0.00 | 0.00 | 0.00 | 0.00 | 0.00 | 0.00 | 0.00 | 0.00 | 0.00 | 3.73 | 4.73 | 6.73 | 11.73 | 14.73 | 16.73 | 19.73 |
| 015 x 028 | 8.66 | 0.00 | 0.00 | 0.00 | 0.00 | 0.00 | 0.00 | 0.34 | 1.34 | 2.34 | 3.34 | 5.34 | 6.34 | 8.34 | 13.34 | 16.34 | 18.34 | 21.34 |
| 016 x 016 | 15.87 | 0.00 | 0.00 | 0.00 | 0.00 | 0.00 | 0.00 | 0.00 | 0.00 | 0.00 | 0.00 | 0.00 | 0.00 | 1.13 | 6.13 | 9.13 | 11.13 | 14.13 |
| 016 x 018 | 12.02 | 0.00 | 0.00 | 0.00 | 0.00 | 0.00 | 0.00 | 0.00 | 0.00 | 0.00 | 0.00 | 1.96 | 2.96 | 4.96 | 9.96 | 12.96 | 14.96 | 17.96 |
| 016 x 020 | 9.76 | 0.00 | 0.00 | 0.00 | 0.00 | 0.00 | 0.00 | 0.00 | 0.22 | 1.22 | 2.22 | 4.22 | 5.22 | 7.22 | 12.22 | 15.22 | 17.22 | 20.22 |
| 016 x 022 | 8.28 | 0.00 | 0.00 | 0.00 | 0.00 | 0.00 | 0.00 | 0.72 | 1.72 | 2.72 | 3.72 | 5.72 | 6.72 | 8.72 | 13.72 | 16.72 | 18.72 | 21.72 |
| 016 x 025 | 6.76 | 0.00 | 0.00 | 0.00 | 0.00 | 0.00 | 1.24 | 2.24 | 3.24 | 4.24 | 5.24 | 7.24 | 8.24 | 10.24 | 15.24 | 18.24 | 20.24 | 23.24 |
| 016 x 028 | 5.72 | 0.00 | 0.00 | 0.00 | 0.26 | 1.28 | 2.28 | 3.28 | 4.28 | 5.28 | 6.28 | 8.28 | 9.28 | 11.26 | 16.26 | 19.26 | 21.28 | 24.28 |
| 017 x 017 | 6.40 | 0.00 | 0.00 | 0.00 | 0.00 | 0.60 | 1.60 | 2.60 | 3.60 | 4.60 | 5.60 | 7.60 | 8.60 | 10.60 | 15.60 | 18.60 | 20.60 | 23.60 |
| 017 x 020 | 4.74 | 0.00 | 0.00 | 0.06 | 2.06 | 2.26 | 3.26 | 4.26 | 5.26 | 6.26 | 7.26 | 9.26 | 10.26 | 12.26 | 17.26 | 20.26 | 22.26 | 25.26 |
| 017 x 022 | 4.05 | 0.00 | 0.00 | 0.67 | 2.67 | 2.95 | 3.95 | 4.95 | 5.95 | 6.95 | 7.95 | 9.95 | 10.95 | 12.95 | 17.95 | 20.95 | 22.95 | 25.95 |
| 017 x 025 | 3.33 | 0.00 | 0.00 | 1.00 | 3.00 | 3.67 | 4.67 | 5.67 | 6.67 | 7.67 | 8.67 | 10.67 | 11.67 | 13.67 | 16.67 | 21.67 | 23.67 | 26.67 |
| 017 x 028 | 2.83 | 0.00 | 0.00 | 1.35 | 3.35 | 4.17 | 5.17 | 6.17 | 7.17 | 8.17 | 9.17 | 11.17 | 12.17 | 14.17 | 19.71 | 22.17 | 24.17 | 27.17 |
| 0175 x 0175 | 2.94 | 0.00 | 0.00 | 0.06 | 2.06 | 4.06 | 5.06 | 6.06 | 7.06 | 8.06 | 9.06 | 11.06 | 12.06 | 14.06 | 19.06 | 22.06 | 24.06 | 27.06 |
| 0175 x 020 | 2.33 | 0.00 | 0.00 | 0.67 | 2.67 | 4.67 | 5.67 | 6.67 | 7.67 | 8.67 | 9.67 | 11.67 | 12.67 | 14.67 | 19.67 | 22.67 | 24.67 | 27.67 |
| 0175 x 022 | 2.00 | 0.00 | 0.00 | 1.00 | 3.00 | 5.00 | 6.00 | 7.00 | 8.00 | 9.00 | 10.00 | 12.00 | 13.00 | 15.00 | 20.00 | 23.00 | 25.00 | 28.00 |
| 0175 x 025 | 1.65 | 0.00 | 0.35 | 1.35 | 3.35 | 5.35 | 6.35 | 7.35 | 8.35 | 9.35 | 10.35 | 12.35 | 13.35 | 15.35 | 20.35 | 23.35 | 25.35 | 28.35 |
| 0175 x 028 | 1.41 | 0.00 | 0.59 | 1.59 | 3.59 | 5.59 | 6.59 | 7.59 | 8.59 | 9.59 | 10.59 | 12.59 | 13.59 | 15.59 | 20.59 | 23.59 | 25.59 | 28.59 |

ROUND-BEVEL WIRE, RADIUS OF CURVATURE r=.00375
Torque Angles Manufactured into .022 Slot Bracket

| WIRE SIZE | DEV. ANGLE | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|
| 016 x 016 | N/E | -- | -- | -- | -- | -- | -- | -- | -- | -- | -- | -- | -- | -- | -- | -- | -- | -- |
| 016 x 018 | N/E | -- | -- | -- | -- | -- | -- | -- | -- | -- | -- | -- | -- | -- | -- | -- | -- | -- |
| 016 x 020 | 39.3700 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 016 x 022 | 29.2400 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.76 |
| 016 x 025 | 22.2800 | 0.00 | 0.00 | 0.00 | 0.00 | 0.00 | 0.00 | 0.00 | 0.00 | 0.00 | 0.00 | 0.00 | 0.00 | 0.00 | 0.00 | 2.72 | 4.72 | 7.72 |
| 016 x 028 | 18.2800 | 0.00 | 0.00 | 0.00 | 0.00 | 0.00 | 0.00 | 0.00 | 0.00 | 0.00 | 0.00 | 0.00 | 0.00 | 0.00 | 3.72 | 6.72 | 8.72 | 11.72 |
| 017 x 017 | N/E | -- | -- | -- | -- | -- | -- | -- | -- | -- | -- | -- | -- | -- | -- | -- | -- | -- |
| 017 x 020 | 30.2200 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 017 x 022 | 23.5400 | 0.00 | 0.00 | 0.00 | 0.00 | 0.00 | 0.00 | 0.00 | 0.00 | 0.00 | 0.00 | 0.00 | 0.00 | 0.00 | 0.00 | 1.46 | 3.46 | 5.46 |
| 017 x 025 | 18.2400 | 0.00 | 0.00 | 0.00 | 0.00 | 0.00 | 0.00 | 0.00 | 0.00 | 0.00 | 0.00 | 0.00 | 0.00 | 0.00 | 3.76 | 6.76 | 8.76 | 11.76 |
| 017 x 028 | 15.0600 | 0.00 | 0.00 | 0.00 | 0.00 | 0.00 | 0.00 | 0.00 | 0.00 | 0.00 | 0.00 | 0.00 | 0.00 | 1.94 | 6.94 | 9.94 | 11.94 | 14.94 |
| 0175 x 0175 | N/E | -- | -- | -- | -- | -- | -- | -- | -- | -- | -- | -- | -- | -- | -- | -- | -- | -- |
| 0175 x 020 | 26.2700 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.73 | 3.73 |
| 0175 x 022 | 20.8200 | 0.00 | 0.00 | 0.00 | 0.00 | 0.00 | 0.00 | 0.00 | 0.00 | 0.00 | 0.00 | 0.00 | 0.00 | 0.00 | 1.18 | 4.18 | 6.18 | 9.18 |
| 0175 x 025 | 16.2600 | 0.00 | 0.00 | 0.00 | 0.00 | 0.00 | 0.00 | 0.00 | 0.00 | 0.00 | 0.00 | 0.00 | 0.00 | 0.74 | 5.74 | 8.74 | 10.74 | 13.74 |
| 0175 x 028 | 13.4700 | 0.00 | 0.00 | 0.00 | 0.00 | 0.00 | 0.00 | 0.00 | 0.00 | 0.00 | 0.00 | 0.53 | 1.53 | 3.53 | 8.53 | 11.53 | 13.53 | 16.53 |
| 018 x 018 | 32.5500 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 018 x 020 | 22.6200 | 0.00 | 0.00 | 0.00 | 0.00 | 0.00 | 0.00 | 0.00 | 0.00 | 0.00 | 0.00 | 0.00 | 0.00 | 0.00 | 0.00 | 2.38 | 4.36 | 7.36 |
| 018 x 022 | 18.1800 | 0.00 | 0.00 | 0.00 | 0.00 | 0.00 | 0.00 | 0.00 | 0.00 | 0.00 | 0.00 | 0.00 | 0.00 | 0.00 | 3.82 | 6.82 | 8.82 | 11.82 |
| 018 x 025 | 14.3100 | 0.00 | 0.00 | 0.00 | 0.00 | 0.00 | 0.00 | 0.00 | 0.00 | 0.49 | 1.49 | 3.49 | 4.49 | 2.69 | 7.89 | 10.69 | 12.69 | 15.69 |
| 018 x 028 | 11.9000 | 0.00 | 0.00 | 0.00 | 0.00 | 0.00 | 0.00 | 0.00 | 1.20 | 2.20 | 3.20 | 5.20 | 6.20 | 5.10 | 10.10 | 13.10 | 15.10 | 18.10 |
| 019 x 019 | 18.0700 | 0.00 | 0.00 | 0.00 | 0.00 | 0.00 | 0.00 | 0.00 | 0.00 | 0.00 | 0.00 | 0.84 | 1.84 | 3.84 | 3.93 | 6.93 | 8.93 | 11.93 |
| 019 x 022 | 13.1600 | 0.00 | 0.00 | 0.00 | 0.00 | 0.00 | 0.00 | 0.33 | 1.33 | 2.33 | 3.33 | 5.33 | 6.33 | 8.33 | 8.84 | 11.84 | 13.84 | 16.84 |
| 019 x 025 | 10.5100 | 0.00 | 0.00 | 0.00 | 0.00 | 0.00 | 0.00 | 1.72 | 2.72 | 3.72 | 4.72 | 6.72 | 7.72 | 9.72 | 11.49 | 14.49 | 16.49 | 19.49 |
| 019 x 028 | 8.8000 | 0.00 | 0.00 | 0.00 | 0.00 | 0.00 | 0.00 | 0.00 | 0.00 | 0.89 | 1.89 | 3.89 | 4.89 | 6.89 | 13.20 | 16.20 | 18.20 | 21.20 |
| 0195 x 0195 | 13.70 | 0.00 | 0.00 | 0.00 | 1.65 | 3.65 | 4.65 | 5.65 | 6.65 | 7.65 | 8.65 | 10.65 | 11.65 | 13.65 | 8.30 | 11.30 | 13.30 | 16.30 |
| 0195 x 0220 | 10.78 | 0.00 | 0.00 | 0.16 | 2.16 | 4.16 | 5.16 | 6.16 | 7.16 | 8.16 | 9.16 | 11.16 | 12.16 | 14.16 | 11.20 | 14.22 | 16.22 | 19.22 |
| 0195 x 0250 | 8.67 | 0.00 | 0.00 | 0.92 | 2.92 | 4.92 | 5.92 | 6.92 | 7.92 | 8.92 | 9.92 | 11.92 | 12.92 | 14.92 | 13.33 | 16.33 | 18.33 | 21.33 |
| 0195 x 0280 | 7.28 | 0.00 | 0.00 | 1.59 | 3.59 | 5.59 | 6.59 | 7.59 | 8.59 | 9.59 | 10.59 | 12.59 | 13.59 | 15.59 | 14.72 | 17.72 | 19.72 | 22.72 |
| 020 x 020 | 10.11 | 0.00 | 0.59 | 1.59 | 3.59 | 5.59 | 6.59 | 7.59 | 8.59 | 9.59 | 10.59 | 12.59 | 13.59 | 15.59 | 11.89 | 14.89 | 16.89 | 19.89 |
| 021 x 025 | 3.35 | 0.00 | 0.00 | 0.00 | 1.65 | 3.65 | 4.65 | 5.65 | 6.65 | 7.65 | 8.65 | 10.65 | 11.65 | 13.65 | 18.65 | 21.65 | 23.65 | 26.65 |
| 021 x 028 | 2.84 | 0.00 | 0.00 | 0.16 | 2.16 | 4.16 | 5.16 | 6.16 | 7.16 | 8.16 | 9.16 | 11.16 | 12.16 | 14.16 | 19.16 | 22.16 | 24.16 | 27.18 |
| 0215 x 0215 | 2.06 | 0.00 | 0.00 | 0.92 | 2.92 | 4.92 | 5.92 | 6.92 | 7.92 | 8.92 | 9.92 | 11.92 | 12.92 | 14.92 | 19.92 | 22.92 | 24.92 | 27.92 |
| 0215 x 028 | 1.41 | 0.00 | 0.59 | 1.59 | 3.59 | 5.59 | 6.59 | 7.59 | 8.59 | 9.59 | 10.59 | 12.59 | 13.59 | 15.59 | 20.59 | 23.59 | 25.59 | 28.59 |

Ortho Specialties Stainless Steel Wire
Torque Angles Manufactured into Slot Bracket

| Wire Size | Slot Size | Dev. Angle | 1° | 2° | 3° | 5° | 7° | 8° | 9° | 10° | 11° | 12° | 14° | 15° | 17° | 22° | 25° | 27° | 30° |
|---|---|---|---|---|---|---|---|---|---|---|---|---|---|---|---|---|---|---|---|
| 016 x 016 | 0.02 | 17.92 | 0.00 | 0.00 | 0.00 | 0.00 | 0.00 | 0.00 | 0.00 | 0.00 | 0.00 | 0.00 | 0.00 | 0.00 | 0.00 | 4.06 | 7.06 | 9.06 | 12.06 |
| 016 x 016 | 0.02 | N/E | -- | -- | -- | -- | -- | -- | -- | -- | -- | -- | -- | -- | -- | -- | -- | -- | -- |
| 016 x 018 | 0.02 | 12.37 | 0.00 | 0.00 | 0.00 | 0.00 | 0.00 | 0.00 | 0.00 | 0.00 | 0.00 | 0.00 | 1.63 | 2.63 | 4.63 | 9.63 | 12.63 | 14.63 | 17.63 |
| 016 x 018 | 0.02 | N/E | -- | -- | -- | -- | -- | -- | -- | -- | -- | -- | -- | -- | -- | -- | -- | -- | -- |
| 016 x 020 | 0.02 | 8.82 | 0.00 | 0.00 | 0.00 | 0.00 | 0.00 | 0.00 | 0.16 | 1.16 | 2.16 | 3.16 | 5.16 | 6.16 | 8.16 | 13.16 | 16.16 | 18.16 | 21.16 |
| 016 x 020 | 0.02 | 25.63 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 1.37 | 4.37 |
| 016 x 022 | 0.02 | 7.31 | 0.00 | 0.00 | 0.00 | 0.00 | 0.00 | 0.69 | 1.69 | 2.69 | 3.69 | 4.69 | 6.69 | 7.69 | 9.69 | 14.69 | 17.69 | 19.69 | 22.69 |
| 016 x 022 | 0.02 | 19.10 | 0.00 | 0.00 | 0.00 | 0.00 | 0.00 | 0.00 | 0.00 | 0.00 | 0.00 | 0.00 | 0.00 | 0.00 | 0.00 | 2.90 | 5.90 | 7.90 | 10.90 |
| 016 x 025 | 0.02 | 5.33 | 0.00 | 0.00 | 0.00 | 0.00 | 1.67 | 2.67 | 3.67 | 4.67 | 5.67 | 6.67 | 8.67 | 9.67 | 11.67 | 16.67 | 19.67 | 21.67 | 24.67 |
| 016 x 025 | 0.02 | 12.99 | 0.00 | 0.00 | 0.00 | 0.00 | 0.00 | 0.00 | 0.00 | 0.00 | 0.00 | 0.00 | 1.01 | 2.01 | 4.01 | 9.01 | 12.01 | 14.01 | 17.01 |
| 016 x 028 | 0.02 | 4.33 | 0.00 | 0.00 | 0.00 | 0.00 | 2.67 | 3.67 | 4.67 | 5.67 | 6.67 | 7.67 | 9.67 | 10.67 | 12.67 | 17.67 | 20.67 | 22.07 | 25.67 |
| 016 x 028 | 0.02 | 10.33 | 0.00 | 0.00 | 0.00 | 0.00 | 0.00 | 0.00 | 0.00 | 0.00 | 0.67 | 1.67 | 3.67 | 4.67 | 6.67 | 11.67 | 14.67 | 16.67 | 19.67 |
| 017 x 017 | 0.02 | 8.02 | 0.00 | 0.00 | 0.00 | 0.00 | 0.00 | 0.00 | 0.96 | 1.96 | 2.96 | 3.96 | 5.96 | 6.96 | 8.96 | 13.96 | 16.96 | 18.96 | 21.96 |
| 017 x 017 | 0.02 | N/E | -- | -- | -- | -- | -- | -- | -- | -- | -- | -- | -- | -- | -- | -- | -- | -- | -- |
| 017 x 017 | 0.02 | N/E | -- | -- | -- | -- | -- | -- | -- | -- | -- | -- | -- | -- | -- | -- | -- | -- | -- |
| 017 x 020 | 0.02 | 4.60 | 0.00 | 0.00 | 0.00 | 0.40 | 2.40 | 3.40 | 4.40 | 5.40 | 6.40 | 7.40 | 9.40 | 10.40 | 12.40 | 17.40 | 20.40 | 22.40 | 25.40 |
| 017 x 020 | 0.02 | 21.11 | 0.00 | 0.00 | 0.00 | 0.00 | 0.00 | 0.00 | 0.00 | 0.00 | 0.00 | 0.00 | 0.00 | 0.00 | 0.00 | 0.89 | 3.89 | 6.89 | 9.89 |
| 017 x 020 | 0.02 | N/E | -- | -- | -- | -- | -- | -- | -- | -- | -- | -- | -- | -- | -- | -- | -- | -- | -- |
| 017 x 022 | 0.02 | 3.62 | 0.00 | 0.00 | 0.00 | 1.36 | 3.36 | 4.36 | 5.36 | 6.36 | 7.36 | 8.36 | 10.36 | 11.36 | 13.36 | 18.36 | 21.36 | 23.36 | 26.38 |
| 017 x 022 | 0.02 | 14.71 | 0.00 | 0.00 | 0.00 | 0.00 | 0.00 | 0.00 | 0.00 | 0.00 | 0.00 | 0.00 | 0.00 | 0.29 | 2.29 | 7.29 | 10.29 | 12.29 | 15.29 |
| 017 x 022 | 0.02 | 22.70 | 0.00 | 0.00 | 0.00 | 0.00 | 0.00 | 0.00 | 0.00 | 0.00 | 0.00 | 0.00 | 0.00 | 0.00 | 0.00 | 0.00 | 2.30 | 4.30 | 7.30 |
| 017 x 025 | 0.02 | 2.78 | 0.00 | 0.00 | 0.22 | 2.22 | 4.22 | 5.22 | 6.22 | 7.22 | 8.22 | 9.22 | 11.22 | 12.22 | 14.22 | 19.22 | 22.22 | 24.22 | 27.22 |
| 017 x 025 | 0.02 | 10.69 | 0.00 | 0.00 | 0.00 | 0.00 | 0.00 | 0.00 | 0.00 | 0.00 | 0.31 | 1.31 | 3.31 | 4.31 | 6.31 | 11.31 | 14.31 | 16.31 | 19.31 |
| 017 x 025 | 0.02 | 15.52 | 0.00 | 0.00 | 0.00 | 0.00 | 0.00 | 0.00 | 0.00 | 0.00 | 0.00 | 0.00 | 0.00 | 0.00 | 1.46 | 6.46 | 9.46 | 11.46 | 14.46 |
| 017 x 028 | 0.02 | 2.23 | 0.00 | 0.00 | 0.00 | 2.77 | 4.77 | 5.77 | 6.77 | 7.77 | 8.77 | 9.77 | 11.77 | 12.77 | 14.77 | 19.77 | 22.77 | 24.77 | 27.77 |
| 017 x 028 | 0.21 | 8.37 | 0.00 | 0.00 | 0.00 | 0.00 | 0.00 | 0.00 | 0.63 | 1.63 | 2.63 | 3.63 | 5.63 | 6.63 | 8.63 | 13.63 | 16.63 | 18.63 | 21.83 |
| 017 x 028 | 0.02 | 11.92 | 0.00 | 0.00 | 0.00 | 0.00 | 0.00 | 0.00 | 0.00 | 0.00 | 0.00 | 0.08 | 2.08 | 3.08 | 5.08 | 10.08 | 13.08 | 15.08 | 18.08 |
| 018 x 018 | 0.02 | N/E | -- | -- | -- | -- | -- | -- | -- | -- | -- | -- | -- | -- | -- | -- | -- | -- | -- |
| 018 x 018 | 0.02 | N/E | -- | -- | -- | -- | -- | -- | -- | -- | -- | -- | -- | -- | -- | -- | -- | -- | -- |
| 018 x 020 | 0.02 | 15.78 | 0.00 | 0.00 | 0.00 | 0.00 | 0.00 | 0.00 | 0.00 | 0.00 | 0.00 | 0.00 | 0.00 | 0.00 | 1.22 | 6.22 | 9.22 | 11.22 | 14.22 |
| 018 x 020 | 0.02 | N/E | -- | -- | -- | -- | -- | -- | -- | -- | -- | -- | -- | -- | -- | -- | -- | -- | -- |
| 018 x 022 | 0.02 | 11.10 | 0.00 | 0.00 | 0.00 | 0.00 | 0.00 | 0.00 | 0.00 | 0.00 | 0.00 | 0.90 | 2.90 | 3.90 | 5.90 | 10.90 | 13.90 | 16.90 | 18.90 |
| 018 x 022 | 0.02 | 19.09 | 0.00 | 0.00 | 0.00 | 0.00 | 0.00 | 0.00 | 0.00 | 0.00 | 0.00 | 0.00 | 0.00 | 0.00 | 0.00 | 2.91 | 5.91 | 7.91 | 10.91 |
| 018 x 025 | 0.02 | 7.86 | 0.00 | 0.00 | 0.00 | 0.00 | 0.00 | 0.14 | 1.14 | 2.14 | 3.14 | 4.14 | 6.14 | 7.14 | 9.14 | 14.14 | 17.14 | 19.14 | 22.14 |
| 018 x 025 | 0.02 | 12.66 | 0.00 | 0.00 | 0.00 | 0.00 | 0.00 | 0.00 | 0.00 | 0.00 | 0.00 | 0.00 | 1.34 | 2.34 | 4.34 | 9.34 | 12.34 | 14.34 | 17.34 |
| 018 x 028 | 0.02 | 6.25 | 0.00 | 0.00 | 0.00 | 0.00 | 0.75 | 1.75 | 2.75 | 3.75 | 4.75 | 5.75 | 7.75 | 8.75 | 10.75 | 15.75 | 18.75 | 20.75 | 23.75 |
| 018 x 028 | 0.02 | 9.88 | 0.00 | 0.00 | 0.00 | 0.00 | 0.00 | 0.00 | 0.00 | 0.12 | 1.12 | 2.12 | 4.12 | 5.12 | 7.12 | 12.12 | 16.12 | 17.12 | 20.12 |
| 019 x 019 | 0.02 | 12.83 | 0.00 | 0.00 | 0.00 | 0.00 | 0.00 | 0.00 | 0.00 | 0.00 | 0.00 | 0.00 | 1.17 | 2.17 | 4.17 | 9.17 | 12.17 | 14.17 | 17.17 |
| 019 x 019 | 0.02 | N/E | -- | -- | -- | -- | -- | -- | -- | -- | -- | -- | -- | -- | -- | -- | -- | -- | -- |
| 019 x 025 | 0.02 | 4.78 | 0.00 | 0.00 | 0.00 | 0.22 | 2.22 | 3.22 | 4.22 | 5.22 | 6.22 | 7.22 | 9.22 | 10.22 | 12.22 | 17.22 | 20.22 | 22.22 | 26.22 |
| 019 x 025 | 0.02 | 9.36 | 0.00 | 0.00 | 0.00 | 0.00 | 0.00 | 0.00 | 0.00 | 0.64 | 1.64 | 2.64 | 4.64 | 5.64 | 7.64 | 12.64 | 15.64 | 17.64 | 20.64 |
| 020 x 025 | 0.02 | 6.90 | 0.00 | 0.00 | 0.00 | 0.00 | 0.10 | 1.10 | 2.10 | 3.10 | 4.10 | 5.10 | 7.10 | 8.10 | 10.10 | 15.10 | 18.10 | 20.10 | 23.10 |
| 021 x 025 | 0.02 | 3.25 | 0.00 | 0.00 | 0.00 | 1.75 | 3.75 | 4.75 | 5.75 | 6.75 | 7.75 | 8.75 | 10.75 | 11.75 | 13.75 | 16.75 | 21.75 | 23.75 | 26.75 |

FIG. 17

PREADJUSTED ORTHODONTIC BRACKET SYSTEM AND METHOD

This is a continuation-in-part of Ser. No. 08/148,974, filed Nov. 8, 1993, now U.S. Pat. No. 5,464,347.

TECHNICAL FIELD

The present invention relates to an improved preadjusted orthodontic bracket system and method, and more particularly, to a system and method for improving edgewise orthodontic bracket and archwire techniques by providing an accurate, measurable, consistent and practical manner for applying the ideal torques desired by clinicians.

BACKGROUND OF THE INVENTION

The term "edgewise" refers to an orthodontic bracket with a rectangular archwire slot designed so that a square or rectangular archwire has to be inserted with its long side dimension placed horizontally into the bracket slot. Early edgewise appliances incorporated very few or no built-in preadjustments and required that tooth movement be achieved by placing complex bends into archwires by individual orthodontic practitioners. This "wire bending" technique led to difficulty in treatment, particularly in the areas of time expended per patient and in the reproducibility of results.

In response to these difficulties and inconsistencies in treatment results, the Andrews technique was developed as the first fully preadjusted and integrated "straight-wire" appliance system. The Andrews preadjusted system essentially has all the necessary angles and planes of movement—commonly referred to as "tip," "torque," "in-out" and "anti-rotation"—manufactured directly into the brackets which, when properly placed on the crown, are intended to eliminate or substantially reduce the need for wire bending by the practitioner to achieve desired tooth movements. These straight-wire appliances are, theoretically, designed to allow the force and resilience of unbent archwires to work with the preadjustments to guide teeth into ideal positions.

Tremendous professional acceptance and commercial success of the Andrews straight-wire appliance system led to the development and manufacture of various competitive preadjusted bracket systems. These include the Roth, Alexander, Hilgers, Bench, Ricketts and Cetlin techniques.

Contemporary appliance system designers strive to identify the proper position desired for each tooth at the conclusion of fixed appliance therapy so that the individual brackets may be pre-built to provide, in conjunction with an archwire, theoretically appropriate alignment forces to a respective tooth. For example, if a designer desires seven degrees of crown torque, then a seven degree torque angle has been built into the individual edgewise bracket by cutting, casting, molding, metal injection molding, or other method of manufacturing bracket slots, stems and/or bases. It is generally presumed by bracket designers and orthodontic practitioners that the desired degree of corrective movement will be expressed by placing a "full-size" rectangular archwire (i.e., an archwire that has its smallest side dimension within 0.001 inch of the width of the bracket slot) into the bracket slot, thus allowing the force and resiliency of the archwire to move the tooth to the desired predetermined position.

The amount of torque actually expressed by a bracket, however, is highly dependent upon wire choice. Round archwires, for example, "spin" in an edgewise bracket slot and generate no torque. Rectangular or square wires which are large or small relative to the bracket slot will generate more or less actual torque, respectively, due to a lessening or increase of the wire-to-slot deviation angle—referred to as slot "play." Greater archwire play in the bracket slot leads to a lower actual torque value, while less play leads to a higher actual torque value.

It is not possible to accurately or consistently achieve the full theoretical torques preferred (and subsequently built into the bracket systems) by appliance designers by using commercially available brackets and archwires. This is due in part to the deviation angles which result even from insertion of "full-size" wires into the bracket slots. Some play must generally exist between the archwire and bracket slot, even if the archwire is considered "full-size" relative to the bracket slot, to allow for archwire insertion. This play reduces the actual torque provided by the system from its full and theoretically correct expression. For example, a Roth prescription upper central bracket is manufactured with a built-in +12 degree torque angle to meet the desired +12 degree final crown position. However, when a 0.021 inch×0.025 inch preformed archwire (commonly viewed as being full-sized relative to the 0.022 inch edgewise bracket slot) is placed into the slot, only +9.67 degrees of torque is actually expressed.

Furthermore, commercially available archwires are not perfectly square or rectangular. Generally speaking, a varying degree of "rounding" or "beveling" is nearly always present on the corners of archwires which significantly alter the actual torque expression achieved by preadjusted brackets. Should archwire corner radii of 0.00375 inch be present (which is common for high-precision nitinol wire), the actual torque achieved by the Roth upper central bracket system described above drops from +9.67 to +8.6 degrees. An archwire corner radii of 0.00775 would drop actual torque expression even further to +5.76 degrees.

To compound this problem, many orthodontic companies offer archwires with significantly greater or lesser corner rounding or beveling from wire to wire, which greatly reduces consistency and predictability in the proper expression of torque.

The true side dimensions of the archwire also have an effect on actual torque forces. Generally speaking, archwires are slightly smaller than the stated proportions. For example, a 0.019 inch×0.025 inch nitinol archwire commercially available from Ortho Specialties, Inc. of Hickory Hills, Ill., is more accurately described as 0.01875 inch×0.02475 inch. This reduction in size increases the play between the archwire and the bracket slot and further reduces actual torque from the theoretically desired expression.

Imprecise bracket dimensions also significantly alter the actual torquing potential of any preadjusted edgewise bracket system, particularly when combined with the previously mentioned inconsistencies in archwire form. Bracket systems with a stated slot width of 0.018 inch or 0.022 inch are commonly, even in precise systems, up to 0.002 greater in size. If the actual slot width of a +12 degree built-in torque Roth prescription "0.022" bracket is 0.024 inch, then the actual torque expression with a "full-size" 0.021 inch×0.025 inch archwire with 0.00375 inch corner radii would only be +1.74 degrees. An archwire with 0.00775 inch corner radii in the same example would eliminate all positive crown torque. Surprisingly, this is not an uncommon situation, because many clinicians prefer highly radiused nitinol-type superelastic or multi-stranded braided wires to facilitate insertion into the slot and reduce overall forces applied to the crowns.

Of perhaps even greater concern is the variability of actual slot size from bracket to bracket. This again contributes to an inconsistent, unpredictable and inaccurate actual torque expression which translates into clinical problems when attempting to move teeth to predetermined positions in an efficient and harmonious fashion. For example, a Roth +12 upper left central bracket is designed to deliver the same actual torque value as the adjacent right central. If the slot of the left bracket is indeed 0.022 inch, then the actual torque expression would be +8.65 degrees when using a 0.021× 0.025 archwire with a 0.00375 radii. This can contrast to +1.74 degrees of actual torque in an adjacent right central bracket utilizing the same continuous archwire but having a 0.024 inch dimension slot.

Simply put, the combination of inconsistent slot dimensions and archwire variability leads to inconsistent, unpredictable, inaccurate and generally ineffective actual torque potential relative to the claims of "straight-wire" systems.

Finally, most clinicians refuse to use "full-size" archwires due to the difficulty of inserting them into bracket slots, the deleterious side effects which may occur due to common bracket placement error, and an undesirable increase in wire/slot friction and archwire stiffness. Full-size wires are often difficult to fit into bracket slots unless the slots are in perfect alignment (which is rarely achieved due to limitations in human ability to visualize and place brackets perfectly). Variations in crown anatomy make perfectly aligned placement even more improbable.

Most clinicians, then, do not follow the archwire sequence necessary for "full" expression of the appliance potential because of difficulties in using full-size wires. Despite this, current appliance design is predicated on the theory that the ideal desirable torques are those built into the appliances.

Perhaps the primary reason full-size wires have generally been recommended by appliance developers is because even minor changes in actual bracket dimensions or archwire shapes have a significant impact on actual torque when archwires less than full-size relative to the bracket slot are used. Indeed, the assumption has been that clinicians follow the recommendation of using full-size wires, and that, as a result, wire corner radii or beveling has no influence since only the archwire side surfaces (not the archwire corners) are contacting the bracket slot.

In fact, few orthodontic professionals use full-size wires. The use of common, less than full-size wires, especially in combination with manual wire bending techniques, leads to broad variations in actual torque generation depending on the specific configuration of individual wires and bracket slots. These changes are random in nature, entirely unpredictable by individual clinicians, and tremendously diminish the treatment efficiencies implied by straight-wire designs. Archwire bending also distorts the in-out and angulation preadjustments built into straight-wire systems. Bending torque into archwires, for example, may lead to a reduction in crown angulation. This phenomenon, referred to as "wagon-wheeling," holds that for every 4 degrees of torque introduced through the archwire, one degree of angulation is lost. The orthodontist may therefore be required to retreat aspects of the dentition previously considered corrected, again reducing the efficiency of preadjusted systems.

For the aforementioned reasons, current preadjusted systems do not perform adequately in the torque component.

SUMMARY OF THE INVENTION

It is a primary object of this invention (publicized recently by Ortho Specialties, Inc. as the TRUE TORQUE™ orthodontic system) to provide a functional and practical manner for achieving clinically desired (target) torques using less than full-sized wires with consistent, accurate and predictable results. This is achieved by designing and manufacturing both brackets and archwires with highly specific and non-variable dimensions, and by calculating the archwire play that exists. The built-in torques of the brackets are then modified to compensate for the play between the archwire and bracket slot, allowing correct actual expression of the desired theoretical torques to be achieved using less than full-sized archwires. As some play and resultant deviation angles are presumed to exist between all archwires and bracket slots, the torque angle built into the bracket must exceed the ideal torque desired from each individual bracket. This is a fundamental departure from the known, common approach of building the amount of torque desired directly and specifically into an individual bracket, with little regard to the actual torque that is ultimately expressed.

An advantage of the present invention is that the largely non-variable bracket and archwire shapes allow for a high degree of accuracy and predictability, requiring little or no archwire bending by individual practitioners to achieve the goals espoused by the preadjusted appliance developers. This results in greater efficiency for the orthodontist and staff, and reduces overall treatment time for the patient.

A further advantage is the ease of archwire insertion because of the use of wires that are less than full-size relative to the bracket slot. Still further advantages of using less than full-size archwires are that bracket positioning errors are not expressed as dramatically and detrimentally and that there is a dramatic reduction in friction between the archwire and the bracket slot. The increase in the ability of the bracket to "slide" along the archwire (referred to as "sliding mechanics" among orthodontic professionals) is a highly desirable method for increasing the efficiency of the appliance and decreasing overall treatment time for the patient.

Another advantage of less than full-size wire engagement is that the stiffness of archwires between bracket slots is reduced.

A further advantage related to proper actual torque expression without wire bending is the reduction in angulation and in-out problems, such as wagon-wheeling, that are created when archwires are torqued manually.

Additional objects, features and advantages of the invention will be apparent from the following detailed description.

BRIEF DESCRIPTION OF THE DRAWINGS

The detailed description particularly refers to the accompanying figures, in which:

FIG. 8 is a chart illustrating actual torque forces generated using a bracket having a 0.020 inch slot width with various sizes of square and rectangular wires, using the common, but generally unreliable, assumption of perfectly square or rectangular archwires;

FIG. 9 is a chart similar to FIG. 8, but illustrating actual torque forces generated using a bracket having a 0.018 inch slot width;

FIG. 10 is a chart similar to FIG. 8, but illustrating actual torque forces generated using a bracket having a 0.022 inch slot width;

FIG. 11 is a chart illustrating actual torque forces generated using a bracket having a 0.020 inch slot width with various sizes of square and rectangular wires, using the less common, but more reliable, assumption of 0.00375 beveled edge archwire corner radii;

FIG. 12 is a chart similar to FIG. 11, but illustrating actual torque forces generated using a bracket having a 0.018 inch slot width;

FIG. 13 is a chart similar to FIG. 11, but illustrating actual torque forces generated using a bracket having a 0.022 inch slot width;

FIG. 14 is a chart illustrating actual torque forces generated using a bracket having a 0.020 inch slot width with various sizes of square and rectangular wires using the less common, but more reliable, assumption of 0.00375 rounded archwire corner radii;

FIG. 15 is a chart similar to FIG. 14, but illustrating actual torque forces generated using a bracket having a 0.018 inch slot width;

FIG. 16 is a chart similar to FIG. 14, but illustrating actual torque forces generated using a bracket having a 0.022 inch slot width;

FIG. 17 is a chart illustrating actual torque forces generated using brackets having various slot widths and using various sizes of precisely measured square and rectangular stainless steel wires available from Ortho Specialties, Inc.

DESCRIPTION OF THE PREFERRED EMBODIMENTS

While the invention will be described in connection with certain preferred embodiments, it will be understood that it is not intended to limit the invention to these particular embodiments. On the contrary, it is intended to cover all alternatives, modifications, and equivalents included within the spirit and scope of the invention as defined by the appended claims.

Figure 1:
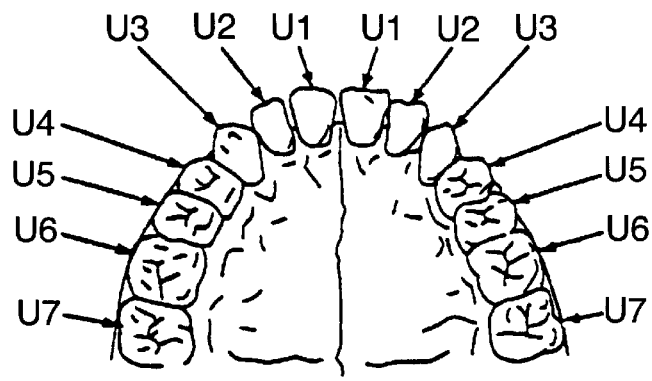
FIG. 1 is a plan view of a set of upper permanent teeth.
Figure 2:
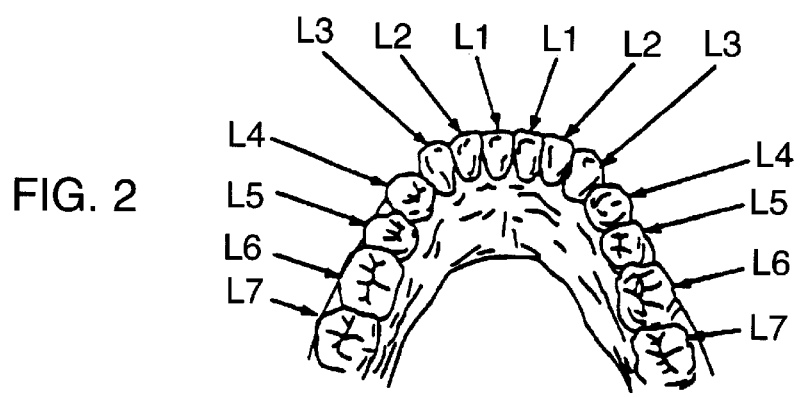
FIG. 2 is a plan view of a set of lower permanent teeth.

Turning now to the drawings and referring first to FIG. 1, there is shown a set of upper permanent teeth, including central teeth (labeled U1), lateral teeth (U2), cuspids (U3), first and second bicuspids (U4 and U5) and first and second molars (U6 and U7). Similarly, FIG. 2 illustrates a set of lower permanent teeth, including central teeth (labeled L1), lateral teeth (L2), cuspids (L3), first and second bicuspids (L4 and L5), and first and second molars (L6 and L7). Lower centrals and laterals are known collectively as lower anteriors.

The present invention relates to preadjusted orthodontic bracket systems and methods for straightening upper and lower permanent teeth. It should be noted that the TRUE TORQUE™ orthodontic bracket system of the present invention is not a new orthodontic technique. Rather, it is a system and method for accurately, predictably and efficiently replicating the torques desired, but not accurately reproduced, in currently existing orthodontic techniques.

Orthodontic brackets are generally applied to the teeth by banding or by gluing their bonding bases directly to the teeth in conventional fashion. Early orthodontic brackets did not incorporate any type of preadjustments. Therefore, after a bracket was banded or bonded to a tooth, an orthodontist was required to bend archwires to be placed in the bracket slot to control and direct movement of the tooth. In contrast, modern bracket systems include brackets having slots aligned at angles and inclinations, varying base thicknesses, and incorporated anti-rotations, thus greatly reducing or eliminating the need for bending wires.

Figure 3:
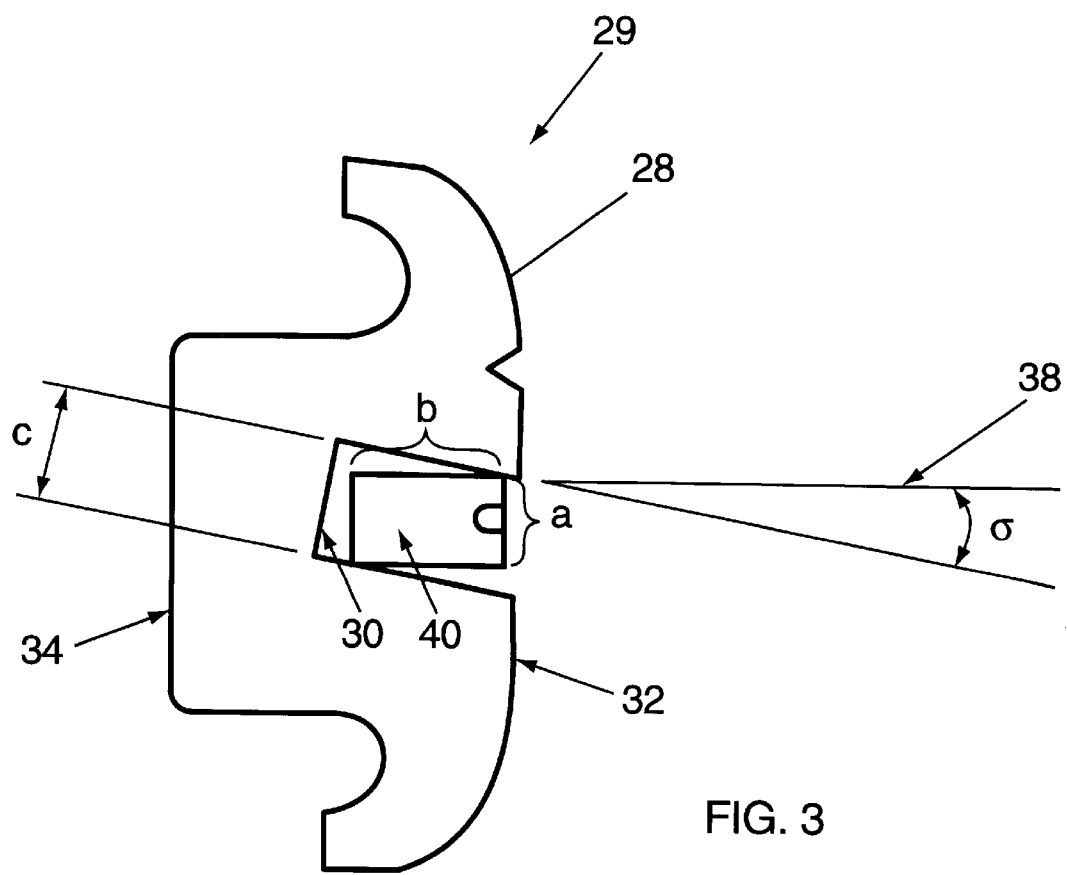
FIG. 3 is a cross-sectional view of an orthodontic bracket, illustrating a slot aligned at a built-in torque angle and an archwire having a square or rectangular cross-section positioned edgewise in the slot.

This invention is related to torque, which is also known to the orthodontist as inclination or third order bends. Torque inclination is illustrated in FIG. 3. An orthodontic bracket 29 includes tie wings 28 and is formed to include a substantially rectangular-shaped slot 30. The bracket includes a front surface 32 and a rear surface 34 designed for attachment to a bonding pad or band, by means of which the bracket is secured on a particular tooth. Slot 30 is formed at a built-in angle σ (known as the torque angle for bracket 29) relative to an imaginary line 38 perpendicular to the rear surface 34 of the bracket. Slot 30 is configured to edgewise receive a substantially rectangular cross-sectioned archwire 40. It should be noted for purposes of the present invention that the term "substantially rectangular archwire" is intended to include both rectangular and square archwire, as well as rectangular and square archwire having "rounded" or "beveled" corners.

Figures 4, 5:
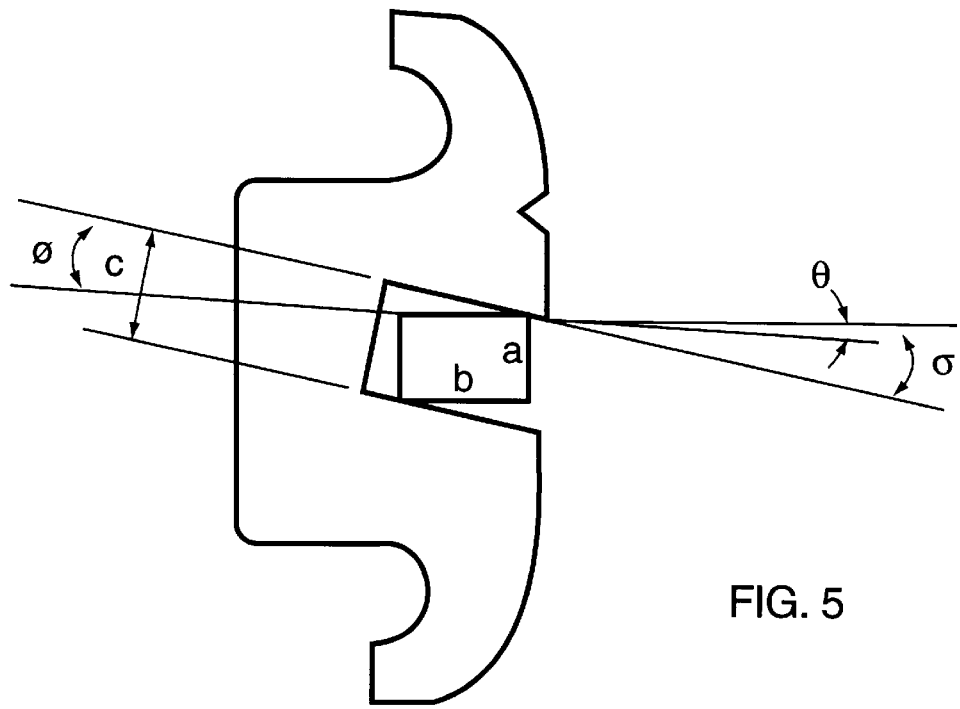
FIG. 4 is a table listing torque angles preformed into various available conventional bracket systems.
FIG. 5 is a cross-sectional view of a bracket and archwire illustrating a plurality of variables used to calculate effective torque angles for an archwire assumed to be perfectly rectangular or square.

The engagement between wire 40 and the side walls defining slot 30 applies a torque force to the tooth on which the bracket is mounted. Different torque angles are typically formed into the respective brackets for various teeth so as to apply a different torque force to each tooth. The built-in torque angle for each tooth depends upon the conventional orthodontic technique for which a bracket is designed. The torque angles preformed into brackets for conventional orthodontic techniques are shown in the table of FIG. 4.

In accordance with an important aspect of the present invention, the torque angle σ and the slot width c of a bracket are designed so that, when the bracket is used with a specifically-manufactured archwire, a conventional orthodontic technique may be replicated as to its theoretically desired embodiment accurately, predictably, efficiently and easily. This is due to precise consideration of the slot width and archwire dimensions (including corner radii) and of the actual torque forces generated. The magnitude of the actual torque forces applied to a tooth is based upon the torque angle σ built into the respective bracket 29, the long cross-sectional dimension b and the short cross-sectional dimension a of the rectangular wire 40, and the width c of the archwire slot 30. The actual (or effective) torque force angle Θ is determined by subtracting "slot play" (i.e., the deviation angle φ) in a bracket/wire combination from the built-in torque angle σ. FIG. 5 illustrates these different angles.

The built-in torque angle σ is known (or can be readily determined) for a given bracket, and, if it is assumed that the archwire is perfectly square or rectangular, the deviation angle φ for the bracket/wire combination can be calculated by the formula:

$$\phi = \text{ARCSIN}\left[\frac{bc - a\sqrt{a^2 + b^2 - c^2}}{a^2 + b^2}\right]. \quad (1)$$

Thus, the effective torque angle Θ can be easily determined, since $$\Theta = \sigma - \phi. \quad (2)$$

Conversely, it will be appreciated that once the effective (target) torque angle Θ recommended by a selected orthodontic technique is determined, and if the precise dimensions of a rectangular archwire and of a bracket slot are measured, then calculations can be made of both the deviation angle φ and the necessary built-in torque angle σ for achieving the target torque angle.

Figure 6:
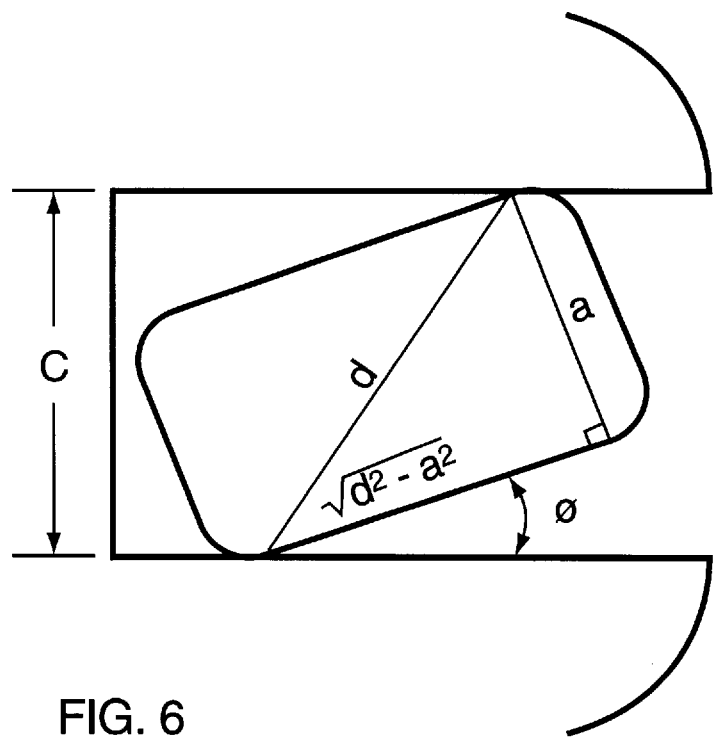
FIG. 6 is a cross-sectional view of a bracket slot and archwire illustrating a plurality of variables used to calculate effective torque angles for an archwire having rounded edges.

The formula (1) above, which is based on an assumption of perfectly square or rectangular wire, has been supplemented with a more accurate formula that takes into consideration wire corner rounding, which is common in available archwires. In this formula, compensation is made for rounded edges on the square or rectangular wire (as shown in FIG. 6), and the deviation angle φ is calculated as:

$$\phi = \text{ARCSIN}\left[\frac{c\sqrt{d^2 - a^2} - a\sqrt{d^2 - c^2}}{d^2}\right]. \quad (3)$$

Figure 7:
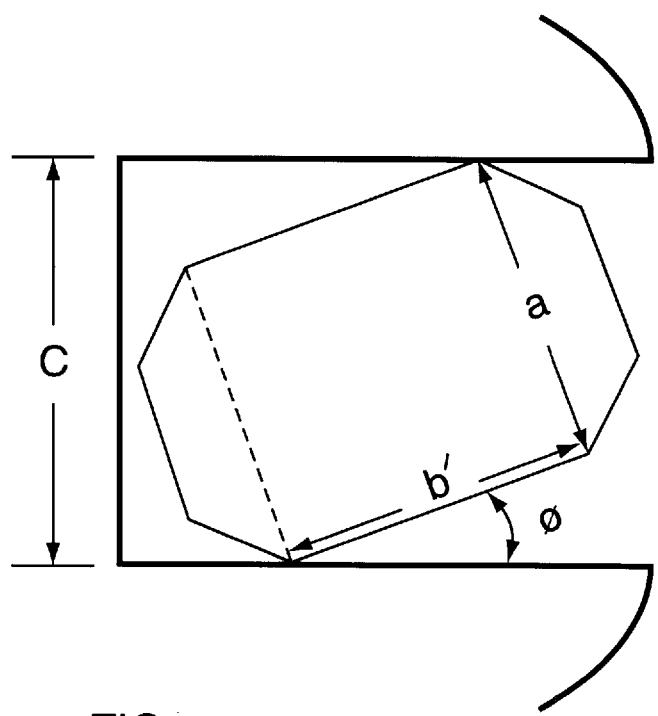
FIG. 7 is a cross-sectional view similar to FIG. 6 illustrating a plurality of variables used to calculate effective torque angles for an archwire having beveled edges.

If the square or rectangular wire used has beveled edges (as shown in FIG. 7), formula (1) above is used to calculate the deviation angle φ. In this instance, however, the reduced long side dimension b' is measured and applied in formula (1) in place of the variable "b."

It will thus be appreciated that, in accordance with the present invention, a bracket intended for use with a specific, less than full-size archwire can be designed such that it has a built-in torque angle σ greater than a full expression of the target torque angle Θ and yet, in combination with the specific archwire, applies force to the tooth at an actual torque angle which substantially corresponds (i.e., within ±2 degrees) to the target torque angle.

In contrast, current bracket systems cannot generate the torques recommended by the developing clinicians due to the deviation angles that necessarily exist. Some play must exist between the archwire and bracket slot to allow for archwire insertion, and this play reduces torque from the theoretically correct levels of expression. Wire "rounding" and/or "beveling" further reduces the actual torque expression in full-size wires, thus further reducing the accuracy of preadjusted bracket systems that rely specifically on built-in torque values for proper appliance expression. The TRUE TORQUE™ concept and resultant bracket systems compensate accurately for these variables to ensure the correct expression of actual torquing forces in the clinical environment.

FIGS. 8–10 are charts which presume perfectly square or rectangular archwires and list actual torque forces generated using, respectively, a 0.020 inch bracket slot width, a 0.018 inch slot width and a 0.022 inch slot width. The torque angle manufactured into the bracket is listed at the top of each column, and the different rows illustrate various wire sizes which may potentially be selected for use with the respective slot system. An "N/E" entry appearing in a "Deviation Angle" column is an indication that the particular archwire "spins" (i.e., achieves no engagement) in the bracket slot because it is too small.

Conventional bracket systems use either the 0.018 inch width slot or the 0.022 inch width slot. In contrast, the TRUE TORQUE™ system employs an 0.020 inch bracket slot width as the preferred embodiment, because the proper diameter and subsequent balance of resilience and stiffness in a finishing square or rectangular orthodontic archwire is most easily achieved with this slot width in most techniques. The present invention is not, however, limited to this or any other slot width choice.

The charts of FIGS. 11, 12 and 13 contain the same type of information as FIGS. 8, 9 and 10, but account for the manufacturing phenomenon termed wire "beveling." Beveling, in which the corners of the square and rectangular archwires appear to be formed at roughly 45 degree angles relative to the top and side portions of the archwire, is a more common form of wire than the perfectly square or rectangular form referred to above.

The charts of FIGS. 14, 15 and 16 again contain the same type of information as FIGS. 8–13, but account for the manufacturing phenomenon termed wire "rounding." Wire rounding assumes generally circular corner radii, often of varying diameters, that can be controlled through means of production.

The preferred embodiment for this system relies on a precise mathematical representation for the preferred 0.018× 0.025 archwire. Just as there is no perfect bracket slot or perfectly square or rectangular archwire, there is also no perfect corner radii for individual archwires. Most wires exhibit properties of both beveling and radii in the corner, and the top and side walls of archwires are generally less than the stated dimensions. To ensure the greatest degree of clinical accuracy that is commercially feasible, various archwires manufactured for this system were measured in order to calculate the amount of deviation, or play, that will occur upon insertion into a specific bracket slot. It is intended that subsequent archwires manufactured for the TRUE TORQUE™ systems will substantially conform to the desired shapes. FIG. 7 illustrates generally the cross-sectional shape of stainless steel archwires provided by Ortho Specialties, Inc. for use in TRUE TORQUE™ systems. The preferred 0.018×0.025 wire for an 0.020 slot is manufactured under close tolerances to have approximately a short side dimension a =0.018 inch and a long side dimension b'=0.0202 inch.

FIG. 17 contains the same type of information as FIGS. 8–16, except that it is based upon use of brackets with a variety of slot widths and use of precisely-measured stainless steel square and rectangular archwires available from Ortho Specialties, Inc. (having the general cross-sectional configuration illustrated in FIG. 7).

Figure 18B:
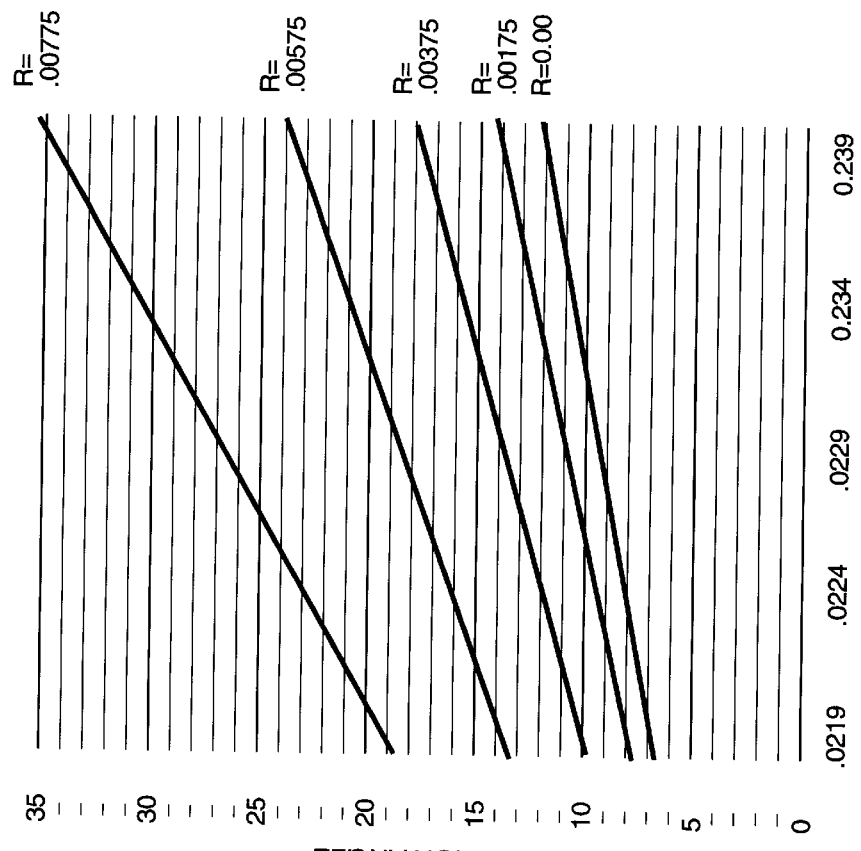
FIGS. 18A and 18B are charts illustrating the relationship between slot widths, archwire corner radii and deviation angles.
Figure 18A:
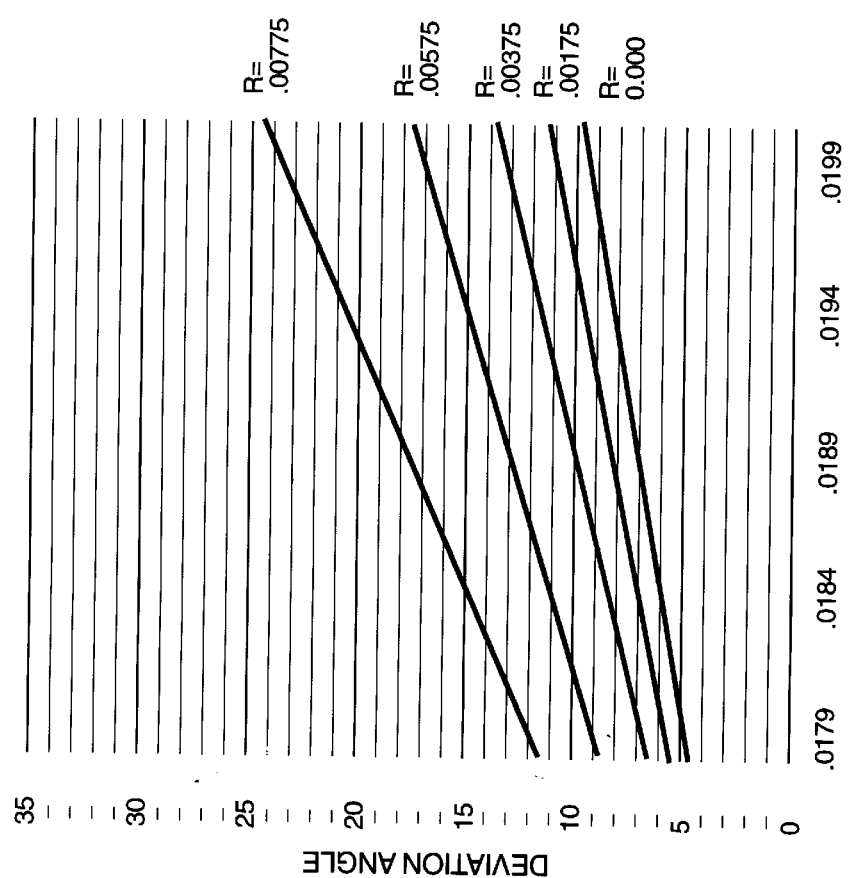

For the purposes of this invention, it is important that specific and largely non-variable slots with specific built-in torque angles are used in conjunction with specific and largely non-variable archwire shapes. This is achieved by cutting, casting, molding, metal injection molding, or other methods of manufacturing brackets slots, stems and/or bracket bases in a highly exacting and non-variable manner (casting is generally preferred because it is most cost effective) to be used in conjunction with wires with a known, highly exacting and non-variable shape. In this way, deviation angles that are necessarily present when using less than full-size archwires can be accurately determined, so that the appropriate levels of torque can be built into the individual brackets to achieve the proper theoretical torque levels proposed by any appliance developer. With a correct understanding and calculation of deviation angles, less than full-size wires may be employed without the negation or elimination of the torque component. FIGS. 18A and 18B illustrate the relationships between deviation angles, variability of the widths of bracket slots and variability of archwire corner radii.

In accordance with the use of less than full-size archwires, the deviation angles which resulted from the combinations of brackets and Ortho Specialties archwires (see FIG. 17) generally fall in the range between 4 degrees and 14 degrees. More specifically, for the preferred combination of a 0.0206 inch slot width and a 0.018 inch×0.025 inch archwire, the resulting deviation angle is 7.86 degrees. Similarly, for a 0.018 inch slot width, the preferred 0.016 inch×0.025 inch archwire resulted in a deviation angle of 5.33 degrees. And for a 0.022 inch slot width, the preferred 0.019 inch×0.025 inch and 0.020 inch×0.025 inch archwires respectively resulted in deviation angles of 9.36 degrees and 6.90 degrees.

To illustrate the principles involved, and the advantages the current invention provides over presently available orthodontic systems, examples of Andrews and Roth prescriptions and counterpart TRUE TORQUE™ systems follow. For purposes of this exemplary comparison, archwires marketed by Ortho Specialties, Inc. were used in all of the bracket systems, since these are the only wires known by the inventors to have specifically measured dimensions needed to accurately compare the capabilities of each system. Measurements of the "true" bracket slot sizes of the Roth and Andrews brackets were provided by Orthodontic Production and Design (ODP) of San Marcos, Calif. Specifically, the 0.022 inch slots recommended by the Roth and Andrews techniques were determined by ODP to have an average actual vertical dimension of 0.0223 inch, with a tolerance range between 0.0219 and 0.0228. The TRUE TORQUE™ brackets have a preferred actual slot size of 0.0206 inch, with a tolerance range of 0.0204–0.0208 inch.

The Andrews 0.022 prescription has the following torque preadjustments:

| Upper: | Central | Lateral | Cuspid | 1st/2nd Bis | 1st/2nd Mos |
|---|---|---|---|---|---|
| | +7 | +3 | −7 | −7 | −10 |
| Lower: | Anteriors | Cuspid | 1st Bi | 2nd Bi | 1st Mo | 2nd Mo |
| | −1 | −11 | −17 | −22 | −25 | −30 |

The actual torques generated by the Andrews appliances (with a recommended 0.018 inch×0.025 inch rectangular archwire in the 0.0223 inch bracket slots) are:

| Upper | Central | Lateral | Cuspid | 1st/2nd Bis | 1st/2nd Mos |
|---|---|---|---|---|---|
| | 0 | 0 | 0 | 0 | 0 |
| Lower: | Anteriors | Cuspid | 1st Bi | 2nd Bi | 1st Mo | 2nd Mo |
| | 0 | 0 | −3.24 | −8.24 | −11.24 | −16.24 |

Another Andrews effective torque range follows which, although it is not recommended, nor understood to be a common practice, assumes use of a full size (0.021 inch× 0.025 inch) Ortho Specialties archwire in the 0.0223 inch bracket slots:

| Upper | Central | Lateral | Cuspid | 1st/2nd Bis | 1st/2nd Mos |
|---|---|---|---|---|---|
| | +2.73 | 0 | −2.73 | −2.73 | −5.73 |
| Lower: | Anteriors | Cuspid | 1st Bi | 2nd Bi | 1st Mo | 2nd Mo |
| | 0 | −6.73 | −12.73 | −17.73 | −20.73 | −25.73 |

It is clear from these examples that the ideal theoretical torques recommended by the Andrews technique (see FIG. 4) are unattainable with commonly-accepted wire techniques short of archwire bending and modification. Wire bending is the antithesis of straight-wire, and reintroduces the unpredictability, inaccuracy and efficiency problems that straight-wire bracket systems are designed to alleviate.

The TRUE TORQUE™ 0.020 Andrews concept takes into consideration archwire/bracket slot deviation angles and corner wire radii, and builds into the bracket system the following torque angles that lead to the ultimate expression of the ideal and proper actual torques:

| Upper | Central | Lateral | Cuspid | 1st/2nd Bis | 1st/2nd Mos |
|---|---|---|---|---|---|
| | +15 | +11 | −15 | −15 | −18 |
| Lower: | Anteriors | Cuspid | 1st Bi | 2nd Bi | 1st Mo | 2nd Mo |
| | −9 | −19 | −25 | −30 | −33 | −38 |

Assuming actual bracket slot dimensions of 0.0206 inch, when used in combination with the preferred Ortho Specialties 0.018 inch×0.025 inch archwire, the following actual torques resulted with the TRUE TORQUE™ 0.020 Andrews System:

| Upper | Central | Lateral | Cuspid | 1st/2nd Bis | 1st/2nd Mos |
|---|---|---|---|---|---|
| | +7.14 | +3.14 | −7.14 | −7.14 | −10.14 |
| Lower: | Anteriors | Cuspid | 1st Bi | 2nd Bi | 1st Mo | 2nd Mo |
| | −1.14 | −11.14 | −17.14 | −22.14 | −25.14 | −30.14 |

The 0.14 degree difference between the Andrews technique ideal theoretical torques (FIG. 4) and the TRUE TORQUE™ system's actual expression is clinically insignificant. Traditionally, variations of ±2 degrees of torque are deemed largely imperceptible or negligible by clinicians. The current manufacturing objective for TRUE TORQUE™ appliances is to create bracket slots with the previously mentioned target of 0.0206 inch, with a possible variation of between 0.0204 and 0.0208. When using the Ortho Specialties 0.018×0.025 stainless steel archwires, the potential variation in actual torque is thus ±1.31 degrees.

The Roth system is the most popular preadjusted appliance in the world. Pursuant to the Roth technique, overcorrection is built into various planes of movement, primarily including torque, so that the overcorrected detention may relapse, or settle, into ideal occlusion. The built-in torque preadjustments in the Roth 0.022 system are:

| Upper | Central | Lateral | Cuspid | 1st/2nd Bis | 1st/2nd Mos | |
|---|---|---|---|---|---|---|
|  | +12 | +8 | −2 | −7 | −14 | |
| Lower: | Anteriors | Cuspid | 1st Bi | 2nd Bi | 1st Mo | 2nd Mo |
|  | −1 | −11 | −17 | −22 | −27 | −30 |

The actual torques generated by the Roth appliances with a generally recommended 0.021 inch×0.025 inch archwire are as follows:

| Upper | Central | Lateral | Cuspid | 1st/2nd Bis | 1st/2nd Mos | |
|---|---|---|---|---|---|---|
|  | +7.73 | +3.73 | 0 | −2.73 | −9.73 | |
| Lower: | Anteriors | Cuspid | 1st Bi | 2nd Bi | 1st Mo | 2nd Mo |
|  | 0 | −6.73 | −12.73 | −17.73 | −22.73 | −25.73 |

The TRUE TORQUE™ version of Roth, as with Andrews, presumes the use of an Ortho Specialties 0.018 inch×0.025 inch archwire in combination with a 0.0206 inch bracket slot. The adjustments built into the TRUE TORQUE™ Roth 0.020 system brackets are as follows:

| Upper | Central | Lateral | Cuspid | 1st/2nd Bis | 1st/2nd Mos | |
|---|---|---|---|---|---|---|
|  | +20 | +16 | −10 | −15 | −22 | |
| Lower: | Anteriors | Cuspid | 1st Bi | 2nd Bi | 1st Mo | 2nd Mo |
|  | −9 | −19 | −25 | −30 | −35 | −38 |

The following torques resulted with the TRUE TORQUE™ 0.020 Roth system:

| Upper | Central | Lateral | Cuspid | 1st/2nd Bis | 1st/2nd Mos | |
|---|---|---|---|---|---|---|
|  | +12.14 | +8.14 | −2.14 | −7.14 | −14.14 | |
| Lower: | Anteriors | Cuspid | 1st Bi | 2nd Bi | 1st Mo | 2nd Mo |
|  | −1.14 | −11.14 | −17.14 | −22.14 | −27.14 | −30.14 |

Again, these are only a 0.14 degree difference from the ideal torques for a Roth technique (as shown in FIG. 4).

Current plans for the TRUE TORQUE™ system include development of an Idealized technique reflecting crown and occlusal relationships of hundreds of successfully treated orthodontic cases. Estimations of the built-in appliance torques for this Idealized 0.020 system, based on conversations with orthodontists and initial clinical observation are as follows:

| Upper | Central | Lateral | Cuspid | 1st/2nd Bis |
|---|---|---|---|---|
|  | +16 | +13 | −11 | −11 |
| Lower: | Anteriors | Cuspid | 1st Bi | 2nd Bi |
|  | −9 | −13 | −15 | −17 |

The effective torque angles with an Ortho Specialties 0.018 inch×0.025 inch archwire in a 0.0206 inch bracket slot are as follows:

| Upper | Central | Lateral | Cuspid | 1st/2nd Bis |
|---|---|---|---|---|
|  | +8.14 | +5.14 | −3.14 | −3.14 |
| Lower: | Anteriors | Cuspid | 1st Bi | 2nd Bi |
|  | −1.14 | −5.14 | −7.14 | −9.14 |

These, too, only differ from the ideal torques by 0.14 degree.

As can be seen from the foregoing detailed description, the present invention provides an improved preadjusted orthodontic bracket system and method. It provides a functional and practical manner for achieving clinically desired (target) torques using less than full-sized archwires. Substantially greater efficiency results for clinicians using the inventive system, as well as a reduction in overall treatment times for patients.

What is claimed is:

1. An orthodontic bracket system for applying torque force to a selected tooth, the system comprising:
   an archwire of substantially rectangular cross-section having a short side dimension, a long side dimension, and an effective long side dimension which is shorter than the long side dimension;
   a cast bracket configured to be attached to the selected tooth and including a substantially rectangular slot which edgewise receives the archwire, the slot having a predetermined width and being formed in the bracket at a built-in torque angle;
   wherein the short side dimension of the archwire is less than full-size for the width of the bracket slot and the built-in torque angle of the slot is selected based upon the width of the slot and the short side and effective long side dimensions of the archwire so that said built-in torque angle is greater than a full expression of a target torque angle recommended for the tooth by a selected one of the Roth, Andrews, Alexander, Hilgers, Bench, Ricketts, and Cetlin preadjusted orthodontic techniques, and so that the archwire and bracket, in combination, apply force to the tooth at an actual torque angle which substantially corresponds to the target torque angle recommended for the tooth by the selected orthodontic technique.

2. The system of claim 1, wherein the width of the slot is in the range of 0.0204–0.0208 inch and the short side dimension of the archwire is approximately 0.018 inch and the long side dimension of the archwire is approximately 0.025 inch.

3. The system of claim 2, wherein the width of the slot is approximately 0.0206 inch.

4. The system of claim 1, wherein the archwire is made of stainless steel.

5. The system of claim 1, wherein the bracket and the bracket slot are formed by casting.

6. The system of claim 1, wherein the width of the slot is in the range of 0.0184–0.0188 inch and the short side dimension of the archwire is approximately 0.016 inch and the long side dimension of the archwire is approximately 0.025 inch.

7. The system of claim 6, wherein the width of the slot is approximately 0.0186 inch.

8. The system of claim 1, wherein the width of the slot is in the range of 0.0224–0.0228 inch, the short side dimension of the archwire is in the range of about 0.019–0.020 inch and the long side dimension of the archwire is about 0.025 inch.

9. The system of claim 8, wherein the width of the slot is approximately 0.0226 inch.

10. A method of providing an orthodontic bracket system for applying torque force to a selected tooth, including an archwire of substantially rectangular cross-section and a bracket with a substantially rectangular slot for edgewise receiving the archwire, the method comprising the steps of:
selecting a preadjusted orthodontic technique to be applied to the tooth from among, the Roth, Andrews, Alexander, Hilgers, Bench, Ricketts, and Cetlin techniques;
determining the target torque angle recommended by the selected technique for applying torque force to the selected tooth;
determining precisely a short side dimension and an effective long side dimension of the archwire;
selecting a desired width for the bracket slot such that the short side dimension of the archwire is less than full-size for the desired width of the bracket slot;
determining a maximum deviation angle that would result from edgewise placement of the archwire in a bracket slot having the selected desired width; and
casting a bracket, configured to be attached to the selected tooth, with a slot having an actual width which substantially corresponds to the selected desired width, the slot being formed in the bracket at a built-in torque angle which is selected based upon the width of the slot and the short side and effective long side dimensions of the archwire so that it is greater than a full expression of the target torque angle, whereby the built-in torque angle is such that, in conjunction with the deviation angle that results upon edgewise placement of the archwire in the bracket slot, torque force is applied to the tooth at an actual torque angle which substantially corresponds to the target torque angle.

11. The method of claim 10, wherein the step of determining the maximum deviation angle includes determining the magnitude by which corner radii of curvature between adjacent sides of the archwire decrease the length of the longer of the first and second side dimensions of the archwire.

12. The method of claim 10, wherein the step of determining the maximum deviation angle includes determining the magnitude by which corner bevels between adjacent sides of the archwire decrease the length of the longer of the first and second side dimensions of the archwire.

13. The method of claim 10, wherein the archwire and the desired slot width are selected such that the maximum deviation angle is within a range of approximately 4–14 degrees.

14. The method of claim 13, wherein the maximum deviation angle is about 8 degrees.

15. An orthodontic bracket system for applying torque force to at least one selected tooth, the system comprising
an archwire of substantially rectangular cross-section having a short side dimension and an effective long side dimension;
a cast bracket configured to be attached to the at least one selected tooth and including a substantially rectangular, longitudinal slot extending across the presented face of the bracket, the slot having a predetermined width such that the short side dimension of the archwire is less than full-size within the slot, and the slot being formed in the bracket at a built-in torque angle, said torque angle being selected based upon the width of the slot and the short side and effective long side dimensions of the archwire so that it is greater than the full expression of a target torque angle recommended for the at least one tooth by a selected one of the Roth, Andrews, Alexander, Hilgers, Bench, Ricketts, and Cetlin preadjusted orthodontic techniques;
the archwire being received edgewise in said slot so that a force is applied to the at least one tooth at an actual torque angle which substantially corresponds to the target torque angle recommended for the at least one tooth by the selected orthodontic technique.

* * * * *